(12) United States Patent
Ohara et al.

(10) Patent No.: US 9,861,099 B2
(45) Date of Patent: Jan. 9, 2018

(54) COMPOSITION FOR ENHANCING PLANT DISEASE CONTROL EFFECT OF MONOSACCHARIDE

(71) Applicants: MITSUI CHEMICALS AGRO, INC., Chuo-ku, Tokyo (JP); NATIONAL UNIVERSITY CORPORATION KAGAWA UNIVERSITY, Takamatsu-shi, Kagawa (JP)

(72) Inventors: Toshiaki Ohara, Yasu (JP); Kiyoko Tanaka, Yasu (JP); Shuji Ishizaki, Yasu (JP); Shigehiro Kato, Yasu (JP); Kazuya Akimitsu, Kagawa (JP); Ken Izumori, Kagawa (JP)

(73) Assignees: MITSUI CHEMICALS AGRO, INC., Tokyo (JP); NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 0 days.

(21) Appl. No.: 14/775,132

(22) PCT Filed: Mar. 10, 2014

(86) PCT No.: PCT/JP2014/056181
§ 371 (c)(1),
(2) Date: Sep. 11, 2015

(87) PCT Pub. No.: WO2014/142074
PCT Pub. Date: Sep. 18, 2014

(65) Prior Publication Data
US 2016/0037768 A1    Feb. 11, 2016

(30) Foreign Application Priority Data

Mar. 13, 2013 (JP) ................................. 2013-050518

(51) Int. Cl.
*A01N 25/30* (2006.01)
*A01N 43/08* (2006.01)

(52) U.S. Cl.
CPC ............. *A01N 25/30* (2013.01); *A01N 43/08* (2013.01)

(58) Field of Classification Search
None
See application file for complete search history.

(56) References Cited

U.S. PATENT DOCUMENTS

2008/0182752 A1    7/2008   Izumori et al.
2011/0281807 A1    11/2011  Ohara et al.

FOREIGN PATENT DOCUMENTS

| CN | 101243799 A | 8/2008 |
|---|---|---|
| JP | H02-255603 A | 10/1990 |
| JP | H07-258007 A | 10/1995 |
| JP | 2000-041621 A | 2/2000 |
| JP | 2004-300079 A | 10/2004 |
| JP | 2006-8669 A | 1/2006 |
| JP | 2007-099639 A | 4/2007 |
| JP | 2012-153643 A | 8/2012 |
| JP | 2012-167080 A | 9/2012 |
| JP | 2012-188367 A | 10/2012 |
| JP | 2012-188368 A | 10/2012 |
| WO | WO 91/13552 A1 | 9/1991 |
| WO | WO 2010/021121 A1 | 2/2010 |

OTHER PUBLICATIONS

SELFNutritionData, food summary for raw avocados, 2014.*
Dobbs, Storage Stability of Tagatose in Buffer Solutions, Thesis, Dec. 2008.*
Toshiaki, JP 2012188368 A, Oct. 4, 2012, machine translation.*
International Search Report (PCT/ISA/210) dated Apr. 22, 2014, by the Japanese Patent Office as the International Searching Authority for International Application No. PCT/JP2014/056181.
Written Opinion (PCT/ISA/237) dated Apr. 22, 2014, by the Japanese Patent Office as the International Searching Authority for International Application No. PCT/JP2014/056181.
Extended Search Report issued by the European Patent Office in corresponding European Patent Application No. 14763077.6 dated Jul. 25, 2016 (7 pages).
Notification of Reasons for Rejection issued by the Japanese Patent Office in corresponding Japanese Patent Application No. 2015-505463 on Sep. 5, 2017 (10 pages including partial English translation).

* cited by examiner

*Primary Examiner* — Layla D Berry
(74) *Attorney, Agent, or Firm* — Buchanan, Ingersoll & Rooney PC

(57) ABSTRACT

Provided is a composition that enhances the effects of monosaccharides. The composition is a composition comprising a monosaccharide as an active ingredient thereof and comprising at least one or more assistants selected from a nonionic surfactant (excluding acetylene glycol-based surfactants, fluorine-based surfactants and silicone-based surfactants), an anionic surfactant (excluding lignin sulfonate), a cationic surfactant, an amphoteric surfactant, a water-soluble polymer, an amino acid, an amino sugar, a disaccharide alcohol and a salt, and is effective as an agricultural control composition against plant disease, particularly plant disease caused by fungi and plant disease caused by bacteria.

15 Claims, No Drawings

COMPOSITION FOR ENHANCING PLANT DISEASE CONTROL EFFECT OF MONOSACCHARIDE

TECHNICAL FIELD

The present invention relates to a composition that enhances the plant disease control effect of a monosaccharide contained as an active ingredient thereof, by incorporating at least one or more assistants, selected from a specific nonionic surfactant, specific anionic surfactant, cationic surfactant, amphoteric surfactant, water-soluble polymer, amino acid, amino sugar, disaccharide alcohol and salt, into a composition containing a monosaccharide as an active ingredient thereof, a method for controlling plant disease by using that composition, and a method for enhancing the control effects of a monosaccharide on plant disease.

BACKGROUND ART

In the agricultural industry, plant disease control agents, namely agricultural chemicals, are used for the purpose of controlling plant diseases in the manner of fungicides and the like with the objective of reducing labor and stabilizing the quality and yield of agricultural products, and are essential for present-day agriculture in terms of ensuring safe and reliable agricultural products. However, as a result of having frequently or excessively used numerous chemical agents having the same mechanism of action among plant disease control agents to a specific plant disease as a target for control, a phenomenon is occurring in which target plant disease pathogens develop tolerance to agricultural chemicals having that mechanism of action.

On the other hand, there has recently been a growing interest among consumers in agricultural products grown with reduced levels of agricultural chemicals as well as social interest in reducing the environmental effects of chemically synthesized plant disease control agents. Amidst these circumstances, there is a desire for plant disease control agents and plant disease control methods that have less effect on the environment in comparison with conventional chemically synthesized plant disease control agents, have a broad spectrum against various plant diseases, and are effective even against resistant microorganisms for which existing plant disease control agents are no longer effective.

Monosaccharides are sugars that are the constituent elements of polysaccharides or oligosaccharides that cannot be further hydrolyzed, and are typically classified into aldoses, ketoses, sugar alcohols (polyols) and the like according to functional groups contained in their chemical structures. Examples of aldoses include glucose, mannose, allose, altrose, talose, galactose, idose, gulose, ribose, lyxose, xylose, arabinose, erythrose, treose and glyceraldehyde; examples of ketoses include fructose, psicose, tagatose, sorbose, xylulose, ribulose, erythrulose and dihydroxyacetone; examples of sugar alcohols include glucitol, mannitol, altritol, iditol, allitol, galactitol, arabitol, xylitol, ribitol, threitol, erythritol, glycerin, inositol and quercitol. In addition, nearly all of these have D-form and L-form optical isomers.

Some monosaccharides are known to enhance disease resistance in plants when administered to a plant (Patent Documents 1 and 2). In addition, monosaccharides have been reported to be effective as plant disease control agents with respect to actual plants. For example, D-tagatose has been determined to exhibit control effects against diseases caused by obligate parasites, such as microorganisms causing downy mildew (such as *Pseudoperonospora cubensis*, *Plasmopara viticola* or *Peronospora parasitica*), microorganisms causing powdery mildew (such as *Sphaerotheca fuliginea*) or microorganisms causing rust disease (such as *Puccinia recondita*), and diseases caused by oomycetes such as *Phytophthora infestans* or *Pythium* species, and to be useful as plant disease control agents (Patent Document 3). In addition, D-talose has been determined to be effective as a control agent of plant diseases caused by *Magnaporthe grisea, Colletotrichum orbiculare, Alternaria brassicicola, Cochliobolus miyabeanus, Venturia inaequalis, Blumeria graminis* f. sp. *hordei, Sphaerotheca fuliginea, Xanthomonas oryzae* pv. *oryzae, Pseudomonas syringae* pv. *lachrymans* and *Ralstonia solanacearum*, L-fructose has been determined to be effective as a control agent of plant diseases caused by *Colletotrichum orbiculare, Alternaria brassicicola, Pythium* species causing of damping-off of cucumber seedlings, *Pseudomonas syringae* pv. *lachrymans* and *Ralstonia solanacearum*, D-allose has been determined to be effective as a control agent of plant diseases caused by *Magnaporthe grisea, Colletotrichum orbiculare, Alternaria brassicicola, Sphaerotheca fuliginea, Phytophthora infestans, Pseudoperonospora cubensis* and *Pythium* species causing damping-off of cucumber seedlings, D-psicose has been determined to be effective as a control agent of plant diseases caused by *Magnaporthe grisea, Colletotrichum orbiculare, Blumeria graminis* f. sp. *hordei, Sphaerotheca fuliginea, Pseudomonas syringae* pv. *lachrymans* and *Ralstonia solanacearum*, D-galactose has been determined to be effective as a control agent of plant diseases caused by *Rhizoctonia solani, Pythium* species causing damping-off of cucumber seedlings, *Phytophthora infestans* and *Erwinia carotovora* subsp. *carotovora*, D-sorbose has been determined to be effective as a control agent of plant diseases caused by *Pseudomonas syringae* pv. *lachrymans* and *Ralstonia solanacearum*, D-mannose has been determined to be effective as a control agent of plant diseases caused by *Pseudomonas syringae* pv. *lachrymans*, and D-mannitol has been determined to be effective as a control agent of plant diseases caused by *Xanthomonas oryzae* pv. *oryzae* and *Pseudomonas syringae* pv. *lachrymans* (Patent Documents 4 and 5). However, the comparatively high treatment concentrations of these monosaccharides as plant disease control agents, and their inadequate dilutability and dispersibility when dissolving the monosaccharides in a spray solution to prepare chemical agents, have been indicated as problems.

Combinations of D-tagatose with other sugars and substances having bactericidal and/or fungicidal action are described in Patent Document 3 with respect to synergistic control effects resulting from combining monosaccharides with other substances. However, test examples are indicated only for neutral monosaccharides as the other monosaccharides, while there is no description of the efficacy of disaccharides or other sugars.

In addition, surfactants have widely been known to be able to be used to enhance the efficacy of chemical agents used as agricultural chemicals. However, since agricultural chemicals are usually liposoluble compounds and the prior art has attempted to enhance the efficacy of such compounds, which is for a stronger sense of compound-stabilizing efficacy rather than enhancing efficacy.

On the other hand, monosaccharides are compounds that exhibit extremely high water solubility and are present in an equilibrium state of α-pyranose, β-pyranose, α-furanose, β-furanose and linear structures in an aqueous solution, therefore the effects of conventional agricultural chemical assistants on such compounds was completely unknown. Although monosaccharides have been described in Patent Documents 3, 4 and 5 as being effective as plant disease control agents, and it is also described that various surfactants can be used as assistants for enhancing efficacy, there are no test examples regarding the efficacy of actual assistants.

PRIOR ART DOCUMENTS

Patent Documents

Patent Document 1: Japanese Unexamined Patent Publication No. 2004-300079
Patent Document 2: Japanese Unexamined Patent Publication No. 2006-8669
Patent Document 3: PCT/JP2009/003925 (WO 2010/021121)
Patent Document 4: Japanese Unexamined Patent Publication No. 2012-188367
Patent Document 5: Japanese Unexamined Patent Publication No. 2012-188368

DISCLOSURE OF THE INVENTION

Problems to be Solved by the Invention

With the foregoing in view, an object of the present invention is to provide a composition that enhances the plant disease control effects of monosaccharides and a method for controlling plant disease that uses that composition.

Means for Solving the Problems

As a result of conducting plant disease control tests when various organic compounds such as agricultural chemical assistants or natural substances were added to monosaccharides in consideration of the present circumstances as described above, the inventors of the present invention surprisingly found that, by using a monosaccharide in combination with a specific nonionic surfactant, specific anionic surfactant, cationic surfactant, amphoteric surfactant, water-soluble polymer, amino acid, amino sugar, disaccharide alcohol or salt, plant disease control effects of the monosaccharide could be significantly enhanced, the amount of monosaccharide used could be reduced considerably, and efficacy against various plant diseases was enhanced to a degree that could not be predicted from the efficacy of the monosaccharide alone, thereby leading to completion of the present invention.

The present invention relates to the following compositions of (Invention 1) to (Invention 10).

(Invention 1) A composition comprising a monosaccharide as an active ingredient thereof and at least one or more assistants selected from a nonionic surfactant (excluding acetylene glycol-based surfactants, fluorine-based surfactants and silicone-based surfactants), an anionic surfactant (excluding lignin sulfonate), a cationic surfactant, an amphoteric surfactant, a water-soluble polymer, an amino acid, an amino sugar, a disaccharide alcohol and a salt.

(Invention 2) The composition of the aforementioned Invention 1, wherein the monosaccharide is at least one or more selected from D-tagatose, D-allose, D-psicose, D-talose, D-sorbose, D-galactose, L-fructose, D-mannose and D-mannitol.

(Invention 3) The composition of the aforementioned Invention 1 or Invention 2, wherein the monosaccharide is D-tagatose.

(Invention 4) The composition of any of the aforementioned Inventions 1 to 3, wherein the nonionic surfactant is at least one or more selected from polyoxyalkylene alkyl ethers, polyoxyalkylene alkyl amines, alkyl polyglycosides, polyoxyalkylene aryl ethers, glycerin fatty acid esters, polyglycerin fatty acid esters, propylene glycol fatty acid esters, sorbitan fatty acid esters, polyoxyethylene sorbitan fatty acid esters, sucrose fatty acid esters, polyoxyalkylene fatty acid esters, polyoxyethylene-polyoxypropylene block polymers, polyoxyethylene fatty acid bisphenyl ethers, fatty acid diethanolamides and alkyl imidazolines;
the anionic surfactant is at least one or more selected from aryl sulfonates, formalin condensates of aryl sulfonates, α-olefin sulfonates, alkyl sulfonates, alkyl diphenyl ether disulfonates, polyoxyethylene alkyl phenyl ether sulfonates, polyoxyethylene alkyl ether sulfosuccinic acid half esters, alkyl sulfates, sulfosuccinates, polyoxyalkylene aryl ether sulfates, polyoxyalkylene alkyl ether sulfates, polyoxyethylene-polyoxypropylene block polymer sulfates, polyoxyalkylene alkyl ether acetates, polyoxyalkylene aryl ether phosphates, polyoxyalkylene alkyl ether phosphates, polyoxyethylene-polyoxypropylene block polymer phosphates, alkyl phosphate esters, methyl taurates, polycarboxylates and fatty acid salts;
the cationic surfactant is at least one or more selected from alkyl amine salts and quaternary ammonium salts;
the amphoteric surfactant is at least one or more selected from alkyl betaines, alkyl glycines, amine oxides and lecithins;
the water-soluble polymer is at least one or more selected from polyoxyalkylene, dextrin, alpha starch, etherified starch, xanthan gum, guar gum and polyvinylpyrrolidone;
the amino acid is at least one or more selected from L-aspartic acid, L-glutamic acid, glycine, β-alanine and L-pyroglutamic acid;
the amino sugar is at least one or more selected from D-glucosamine hydrochloride and D-galactosamine hydrochloride;
the disaccharide alcohol is at least one or more selected from maltitol, isomaltitol, lactitol and isomalt; and,
in the salt, the cation derived from the base that forms the salt is at least one or more ions selected from sodium, potassium, ammonium, calcium and magnesium.

(Invention 5)
The composition of any of the aforementioned Inventions 1 to 3, wherein the nonionic surfactant is at least one or more selected from polyoxyalkylene alkyl ethers, polyoxyalkylene alkyl amines, alkyl polyglycosides, polyoxyalkylene aryl ethers, glycerin fatty acid esters, polyglycerin fatty acid esters, propylene glycol fatty acid esters, sorbitan fatty acid esters, polyoxyethylene sorbitan fatty acid esters, fatty acid diethanolamides and alkyl imidazolines;
the anionic surfactant is at least one or more selected from aryl sulfonates, formalin condensates of aryl sulfonates, α-olefin sulfonates, alkyl sulfates, sulfosuccinates, polyoxyalkylene aryl ether sulfates, polyoxyalkylene alkyl ether sulfates, polyoxyalkylene alkyl ether acetates, polyoxyalkylene aryl ether phosphates, polyoxyalkylene alkyl ether phosphates, methyl taurates and polycarboxylates; and
in the salt, the anion that forms the salt is derived from hydrochloric acid, sulfuric acid, nitric acid, phosphoric acid, carbonic acid or acetic acid, and the cation derived from a base is at least one or more ions selected from sodium, potassium, ammonium, calcium and magnesium.

(Invention 6)

The composition of any of the aforementioned Inventions 1 to 5, wherein the monosaccharide is D-tagatose; and the anionic surfactant is at least one or more selected from alkyl sulfates, aryl sulfonates and formalin condensates of aryl sulfonates.

(Invention 7) The composition of any of the aforementioned Inventions 1 to 6, which comprises 1 to 95 parts by weight of the monosaccharide based on a total of 100 parts by weight of the composition, and an assistant.

(Invention 8)

The composition of the aforementioned Invention 7, which comprises 5 to 95 parts by weight of D-tagatose; and at least one or more assistants selected from 0.01 to 5 parts by weight of an alkyl sulfate, 0.01 to 5 parts by weight of an aryl sulfonate and 0.01 to 20 parts by weight of a formalin condensate of an aryl sulfonate, based on a total of 100 parts by weight of the composition.

(Invention 9)

The composition of any of the aforementioned Inventions 1 to 8, which is a control agent for a plant disease.

(Invention 10)

The composition of the aforementioned Invention 9, wherein the plant disease is a disease caused by fungi or a disease caused by bacteria.

The present invention also relates to a method for controlling plant disease of the following (Invention 11) to (Invention 13), and a method for enhancing the control effects of a monosaccharide against plant disease of the following (Invention 14) and (Invention 15).

(Invention 11)

A method for controlling plant disease, comprising applying the composition of any of the aforementioned Inventions 1 to 10 to a plant body.

(Invention 12)

The method for controlling plant disease of the aforementioned Invention 11, wherein application to a plant body is carried out by contacting the composition with a plant body or seed, or by contacting with a root or underground stem of a plant by containing in cultivation soil.

(Invention 13)

The method for controlling plant disease of the aforementioned Invention 12, wherein application to cultivation soil is carried out by treating the surface of soil with the composition, irrigating soil with the composition or mixing the composition into the soil.

(Invention 14)

A method for enhancing the control effects of a monosaccharide against plant disease, comprising applying the composition of any of the aforementioned Inventions 1 to 10 to a plant body.

(Invention 15)

A method for enhancing the control effects of a monosaccharide against plant disease, comprising applying a monosaccharide and at least one or more selected from a nonionic surfactant (excluding acetylene glycol-based surfactants, fluorine-based surfactants and silicone-based surfactants), an anionic surfactant (excluding lignin sulfonate), a cationic surfactant, an amphoteric surfactant, a water-soluble polymer, an amino acid, an amino sugar, a disaccharide alcohol and a salt, to a plant body either simultaneously or separately.

Effects of the Invention

The composition of the present invention, which comprises a monosaccharide in combination with at least one or more assistants selected from a specific nonionic surfactant, a specific anionic surfactant, cationic surfactant, amphoteric surfactant, water-soluble polymer, amino acid, amino sugar, disaccharide alcohol and salt, has enhanced plant disease control effects against various plant diseases in comparison with a monosaccharide alone, and has improved stability and dilutability. Consequently, it demonstrates superior effects against various diseases caused by fungi and bacteria, including chemical-resistant microorganisms in the form of a stem and leaf dusting powder, soil treatment agent or seed treatment agent and the like while reducing the amount of monosaccharide used without causing chemical damage to the plant. These effects are facts which could not have been predicted by a person with ordinary skill in the art.

BEST MODE FOR CARRYING OUT THE INVENTION

An arbitrary monosaccharide can be used in the composition of the present invention. More specifically, examples of monosaccharides having D-form or L-form optical isomers include, but are not limited to, glucose, mannose, allose, altrose, talose, galactose, idose, gulose, ribose, deoxyribose, lyxose, xylose, arabinose, erythrose, treose, glyceraldehyde, fructose, psicose, tagatose, sorbose, xylulose, ribulose, erythrulose, glucitol, mannitol, altritol, iditol, arabitol, threitol, rhamnose and fucose; while examples of monosaccharides not having optical isomers include, but are not limited to, dihydroxyacetone, allitol, galactitol, xylitol, ribitol, erythritol and glycerin.

Preferable examples include D-tagatose, D-allose, D-psicose, D-talose, D-sorbose, D-galactose, L-fructose, D-mannose and D-mannitol, and D-tagatose is more preferable.

Nonionic surfactants which can be used in the composition of the present invention are any nonionic surfactants with the exception of acetylene glycol-based surfactants, fluorine-based surfactants and silicone-based surfactants. Specific examples thereof include polyoxyalkylene alkyl ethers (such as polyoxyethylene alkyl ethers, polyoxyethylene castor oil ethers or polyoxyethylene hydrogenated castor oil ethers), polyoxyalkylene alkyl amines (such as polyoxyethylene alkyl amines or polyoxyethylene fatty acid amides), alkyl polyglycosides (such as decyl polyglucoside), polyoxyalkylene aryl ethers (such as polyoxyethylene styryl phenyl ether, polyoxyethylene alkyl phenols, polyoxyalkylene styryl phenyl ethers, polyoxyethylene benzyl phenyl ether, polyoxyalkylene benzyl phenyl ethers, formalin condensates of polyoxyethylene styryl phenyl ether, polyoxyethylene dialkyl phenyl ethers or formalin condensates of polyoxyethylene alkyl phenyl ethers), glycerin fatty acid esters (such as fatty acid mono- or diglycerides such as glycerin monopalmitate, glycerin monostearate, glycerin monobehenate, glycerin mono-12-hydroxystearate, glycerin monooleate, glycerin monocaprylate, glycerin monocaprate, glycerin monolaurate, glycerin mono- or distearate, glycerin mono- or dipalmitate, glycerin mono- or dibehenate, glycerin mono- or dioleate, glycerin diacetomonolaurate or glycerin diacetomonooleate; glycerin organic acid fatty acid esters such as acetic acid fatty acid monoglycerides, citric acid fatty acid monoglycerides, succinic acid fatty acid monoglycerides, lactic acid fatty acid monoglycerides or diacetyltartaric acid fatty acid monoglycerides; acetylated monoglycerides; or medium-chain fatty acid triglycerides), polyglycerin fatty acid esters (such as diglycerin monostearate, diglycerin monolaurate, diglycerin monomyristate, diglycerin monostearate, diglycerin monooleate, tetraglycerin stearate, decaglycerin laurate or polyglycerin polyricinoleate), propylene glycol fatty acid esters (such as propylene glycol monolaurate, propylene glycol monopalmitate, propylene glycol monostearate or propylene glycol monooleate), sorbitan fatty acid esters (such as sorbitan monolaurate, sorbitan monopalmitate, sorbitan monostearate, sorbitan tristearate or sorbitan monooleate), polyoxyethylene sorbitan fatty acid esters (such as polyoxyethylene sorbitan monolaurate, polyoxyethylene sorbitan monostearate, polyoxyethylene sorbitan tristearate or polyoxyethylene sorbitan oleate), sucrose fatty acid esters (such as sucrose monocaprate or sucrose monolaurate), polyoxyalkylene fatty acid esters (such as polyoxyethylene monolaurate, polyoxyethylene distearate, polyoxyethylene fatty acid esters, polyoxyethylene resin acid esters or polyoxyethylene fatty acid diesters), polyoxyethylene-polyoxypropylene block polymers (such as polyoxyethylene-polyoxypropylene block polymers, alkyl polyoxyethylene-polyoxypropylene block polymer ethers or alkyl phenyl polyoxyethylene-polyoxypropylene block polymer ethers), polyoxyethylene fatty acid bisphenyl ethers, fatty acid diethanolamides and alkyl imidazolines.

Preferable examples of nonionic surfactants include, but are not limited to, polyoxyalkylene alkyl ethers, polyoxyalkylene alkyl amines, alkyl polyglycosides, polyoxyalkylene aryl ethers, glycerin fatty acid esters, polyglycerin fatty acid esters, propylene glycol fatty acid esters, sorbitan fatty acid esters, polyoxyethylene sorbitan fatty acid esters, fatty acid diethanolamides and alkyl imidazolines.

Examples of anionic surfactants which can be used in the composition of the present invention are arbitrary anionic surfactants with the exception of lignin sulfonate, and examples thereof include aryl sulfonates (such as alkyl benzene sulfonates such as sodium dodecyl benzene sulfonate; or alkyl naphthalene sulfonates such as sodium alkyl naphthalene sulfonates, sodium monoalkyl naphthalene sulfonates or sodium dialkyl naphthalene sulfonates), formalin condensates of aryl sulfonates (such as salts of formalin condensates of naphthalene sulfonate such as sodium salts of naphthalene sulfonate formalin condensates; salts of formalin condensates of alkyl naphthalene sulfonates such as sodium salts of alkyl naphthalene sulfonate formalin condensates; or salts of formalin condensates of phenol sulfonates such as sodium salts of phenol sulfonate formalin condensates), α-olefin sulfonates (such as sodium α-olefin sulfonate), alkyl sulfonates (such as sodium alkyl sulfonates), alkyl diphenyl ether disulfonates (such as sodium alkyl diphenyl ether disulfonates), polyoxyethylene alkyl phenyl ether sulfonates (such as sodium polyoxyethylene alkyl phenyl ether sulfonates), polyoxyethylene alkyl ether sulfosuccinic acid half esters, alkyl sulfates (such as sodium lauryl sulfate), sulfosuccinates (such as dialkyl sulfosuccinates), polyoxyalkylene aryl ether sulfates (such as polyoxyethylene alkyl aryl ether sulfates, polyoxyethylene styryl phenyl ether sulfates, polyoxyethylene benzyl phenyl ether sulfates or polyoxyalkylene styryl phenyl ether sulfates), polyoxyalkylene alkyl ether sulfates (such as polyoxyethylene alkyl ether sulfates such as polyoxyethylene lauryl ether sulfate), polyoxyethylene-polyoxypropylene block polymer sulfates (such as sodium polyoxyethylene-polyoxypropylene block polymer sulfates), polyoxyalkylene alkyl ether acetates (such as polyoxyethylene alkyl ether acetates such as sodium polyoxyethylene lauryl ether acetate), polyoxyalkylene aryl ether phosphates (such as polyoxyethylene styrenated phenyl ether phosphate, polyoxyethylene styryl phenyl ether phosphate, polyoxyethylene benzyl phenyl ether phosphate or polyoxyethylene alkyl phenyl ether phosphates), polyoxyalkylene alkyl ether phosphates (such as polyoxyethylene lauryl ether phosphate monoethanolamine salts or polyoxyethylene lauryl ether phosphate esters), polyoxyethylene-polyoxypropylene block polymer phosphates (such as sodium polyoxyethylene-polyoxypropylene block polymer phosphates), alkyl phosphate esters (such as alkyl phosphoric acids or sodium alkyl phosphates), methyl taurates (such as sodium oleyl methyl taurate), polycarboxylates (such as sodium alkylene maleate copolymers, isobutylene maleate copolymers, sodium acrylate maleate copolymers or sodium polycarboxylate-ammonium distyryl phenyl ether sulfate), and fatty acid salts (such as semi-hydrogenated beef tallow fatty acid soda soap).

Preferable examples of anionic surfactants include, but are not limited to, aryl sulfonates, formalin condensates of aryl sulfonates, α-olefin sulfonates, alkyl sulfates, sulfosuccinates, polyoxyalkylene aryl ether sulfates, polyoxyalkylene alkyl ether sulfates, polyoxyalkylene alkyl ether acetates, polyoxyalkylene aryl ether phosphates, polyoxyalkylene alkyl ether phosphates, methyl taurates and polycarboxylates.

An arbitrary cationic surfactant can be used in the composition of the present invention. More specifically, examples thereof include, but are not limited to, alkyl amine salts (such as coconut amine acetate or stearyl amine acetate) and quaternary ammonium salts (such as didecyl dimethyl ammonium chloride, oleylbis(2-hydroxyethyl) methyl ammonium chloride, alkyl trimethyl ammonium chloride, methyl polyoxyethylene alkyl ammonium chloride, alkyl N-methyl pyridinium bromide, alkyl methylated ammonium chloride, alkyl pentamethyl propylene diamine dichloride, alkyl dimethyl benzalkonium chloride, benzethonium chloride and cetyl pyridinium chloride).

An arbitrary amphoteric surfactant can be used in the composition of the present invention. More specifically, examples thereof include, but are not limited to, alkyl betaines (such as lauryl betaine, dialkyl diaminoethyl betaines or alkyl dimethyl benzyl betaines), alkyl glycines (such as dialkyl diaminoethyl glycines or alkyl dimethyl benzyl glycines), amine oxides (such as lauryl dimethyl amine oxide) and lecithins (such as glycerophospholipids such as soybean lecithin or egg yolk lecithin), and alkyl betaine and amine oxides are preferable.

An arbitrary water-soluble polymer can be used in the composition of the present invention. More specifically, examples thereof include, but are not limited to, various types of water-soluble natural polymers, water-soluble semi-synthetic polymers, and water-soluble synthetic polymers such as acrylic polymers (such as sodium polyacrylate, sodium polymethacrylate, copolymers of partially saponified vinyl acetate and vinyl ether, or polymers or copolymers of acrylic acid, methacrylic acid, maleic acid and esters or salts thereof), polyoxyalkylenes (such as polyoxyethylene, polyethylene glycol or polyethylene oxide), cellulose derivatives (such as methyl cellulose, hydroxyethyl cellulose, hydroxypropyl cellulose or hydroxypropyl methyl cellulose), modified starches (such as dextrin, alpha starch, soluble starch, etherified starch or esterified starch), natural polymers (such as xanthan gum, guar gum or sodium alginate) and synthetic polymers (such as polyvinyl alcohol or polyvinylpyrrolidone). Preferable examples include, but are not limited to, polyoxyalkylenes, dextrin, alpha starch, etherified starch, xanthan gum, guar gum and polyvinylpyrrolidone, while more preferable examples include, but are not limited to, etherified starch and xanthan gum.

An arbitrary amino acid can be used in the composition of the present invention. More specifically, examples of amino acids having D- or L-form optical isomers include alanine, valine, leucine, isoleucine, phenylalanine, tyrosine, tryptophan, serine, threonine, cysteine, cystine, methionine, proline, aspartic acid, asparagine, glutamic acid, glutamine, histidine, arginine, lysine, norvaline, homoserine, homocysteine, hydroxyproline, ornithine, citrulline, 3,4-dihydroxyphenylalanine, theanine, pyroglutamic acid and carnitine. Examples of amino acids that do not have optical isomers include glycine, sarcosine, glycine betaine, guanidinoacetic acid, β-alanine, γ-aminobutyric acid, taurine, creatine and 2-aminoisobutyric acid. Preferable examples include, but are not limited to, L-aspartic acid, L-glutamic acid, glycine, β-alanine and L-pyroglutamic acid.

An arbitrary amino sugars or salt thereof can be used in the composition of the present invention. Specific examples of salts include hydrochlorides and sulfates. More specifically, examples of amino sugars include, but are not limited to, D-glucosamine, D-glucosamine hydrochloride, N-acetyl-D-glucosamine, D-galactosamine, D-galactosamine hydrochloride, N-acetyl-D-galactosamine, D-mannosamine, D-mannosamine hydrochloride and N-acetyl-D-mannosamine, while preferable examples include, but are not limited to, D-glucosamine hydrochloride and D-galactosamine hydrochloride.

An arbitrary disaccharide alcohol can be incorporated in the composition of the present invention. More specifically, examples thereof include, but are not limited to, maltitol, isomaltitol, lactitol and isomalt (palatinit).

An arbitrary salt, obtained by ionic bonding between an acid and ion derived from a base, can be used in the composition of the present invention. Preferably, a salt in which the cation derived from the base that forms the salt is either sodium, potassium, ammonium, calcium or magnesium, and more preferably, any of a normal salt, acidic salt or basic salt can be used in which the anion that forms the salt is derived from either hydrochloric acid, sulfuric acid, nitric acid, phosphoric acid, carbonic acid or acetic acid. Specific examples thereof include, but are not limited to, $NaCl$, $NaHSO_4$, $Na_2SO_4$, $NaHCO_3$, $Na_2CO_3$, $NaNO_3$, $NaH_2PO_4$, $Na_2HPO_4$, $Na_3PO_4$, $CH_3CO_2Na$, $KCl$, $KHCO_3$, $K_2CO_3$, $KHSO_4$, $K_2SO_4$, $KNO_3$, $KH_2PO_4$, $K_2HPO_4$, $K_3PO_4$, $CH_3CO_2K$, $CaCl_2$, $Ca(OH)Cl$, $Ca(NO_3)_2$, $CaSO_4$, $CaHPO_4$, $Ca(H_2PO_4)_2$, $Ca_3(PO_4)_2$, $CaCO_3$, $MgCl_2$, $Mg(OH)Cl$, $Mg(NO_3)_2$, $MgSO_4$, $MgHPO_4$, $Mg(H_2PO_4)_2$, $Mg_3(PO_4)_2$, $MgCO_3$, $NH_4Cl$, $NH_4NO_3$, $(NH_4)_2SO_4$, $NH_4H_2PO_4$, $(NH_4)_2HPO_4$ and $CH_3CO_2NH_4$.

In the composition of the present invention, a monosaccharide and at least one or more assistants, selected from a nonionic surfactant (excluding acetylene glycol-based surfactants, fluorine-based surfactants and silicone-based surfactants), anionic surfactant (excluding lignin sulfonate), cationic surfactant, amphoteric surfactant, water-soluble polymer, amino acid, amino sugar, disaccharide alcohol and salt, can be incorporated at a blending ratio capable of enhancing the control effects of the monosaccharide against plant disease. More specifically, the assistant can be incorporated at a blending ratio of 0.001 to 40 parts by weight based on 1 part by weight of monosaccharide, preferably 0.0025 to 10 parts by weight based on 1 part by weight of monosaccharide, and more preferably 0.005 to 1 part by weight based on 1 part by weight of monosaccharide.

More specifically, in the case of incorporating the aforementioned specific nonionic surfactant, the aforementioned specific anionic surfactant, cationic surfactant, amphoteric surfactant or water-soluble polymer as an assistant, the assistant can be incorporated at a blending ratio of 0.0001 to 40 parts by weight based on 1 part of monosaccharide, preferably 0.001 to 10 parts by weight based on 1 part by weight of monosaccharide, and more preferably 0.0025 to 1 part by weight based on 1 part by weight of monosaccharide.

In addition, in the case of incorporating an amino acid, amino sugar, disaccharide alcohol or salt as an assistant, the assistant can be incorporated at a blending ratio of 0.1 to 5 parts by weight based on 1 part by weight of monosaccharide and preferably 0.5 to 1 part by weight based on 1 part by weight of monosaccharide.

A preferable blending example of the composition of the present invention is a composition containing D-tagatose as monosaccharide; and at least one or more assistants selected from alkyl sulfates, aryl sulfonates and formalin condensates of aryl sulfonates.

A preferable embodiment of a blending example of the composition of the present invention is a composition comprising 1 to 95 parts by weight of monosaccharide, based on a total of 100 parts by weight of the composition; and an assistant, and a more preferable embodiment is a composition comprising 5 to 95 parts by weight of D-tagatose as monosaccharide; and at least one or more assistants selected from 0.01 to 5 parts by weight of an alkyl sulfate, 0.01 to 5 parts by weight of an aryl sulfonate and 0.01 to 20 parts by weight of a formalin condensate of an aryl sulfonate, based on a total of 100 parts by weight of the composition.

The composition of the present invention can be formulated into a desired form by incorporating the aforementioned components in the aforementioned ratios. More specifically, the preparation may be in a form of either a solid preparation such as a powder, water-dispersible powder, water-dispersible granules, water-soluble powder, water-soluble granules or granules; or a liquid preparation such as an emulsion, solution, microemulsion, aqueous suspension preparation, aqueous emulsion preparation or suspoemulsion preparation, and the composition of the present invention can be formulated into a wide range of preparation types. In addition, in the case of a form other than the specific forms exemplified here, the composition can be formulated into an arbitrary preparation that is contacted with a plant body or seeds or contained in cultivation soil either directly or after diluting.

Usually 1 to 95 parts by weight, preferably 40 to 90 parts by weight, and more preferably 60 to 85 parts by weight of the aforementioned monosaccharide can be incorporated as active ingredient in a solid preparation that is a preparation form of the composition of the present invention based on a total of 100 parts by weight of the solid preparation, and the remainder is the aforementioned assistant and various other auxiliary components which can be incorporated as necessary.

Usually 1 to 80 parts by weight, preferably 3 to 50 parts by weight, and more preferably 4 to 20 parts by weight of the aforementioned monosaccharide can be incorporated as active ingredient in a liquid preparation that is a preparation form of the composition of the present invention based on a total of 100 parts by weight of the liquid preparation, and the remainder is the aforementioned assistant and various other auxiliary components which can be incorporated as necessary.

The composition of the present invention may comprise only the aforementioned monosaccharide and assistant in the bulk form, or can be further incorporated with another surfactant usually incorporated in agricultural chemical preparations, solid carriers, liquid carriers, binders, solvents, stabilizers such as an antioxidant or ultraviolet protective agent, pH adjusters such as citric acid or magnesium carbonate, antimicrobials such as sodium benzoate, potassium sorbate, 1,2-benzisothiazolin-3-one or ethylparaben, pigments or various other auxiliary components as necessary.

Examples of other surfactants which can be further used in the composition of the present invention include those indicated below. Examples of nonionic surfactants include silicone-based surfactants; acetylene glycol-based surfactants and fluorine-based surfactants, while examples of anionic surfactants include lignin sulfonate.

A carrier which can be used in the composition of the present invention can be a synthetic or natural inorganic or organic substance that is mixed into the composition to assist in delivery of the active ingredient compound to a plant or facilitate storage, transport or handling of the active ingredient. Examples of solid carriers that can be used in the composition of the present invention include those indicated below. Examples thereof include clay, silicate, talc, bentonite, calcium carbonate, zeolite, pumice, diatomaceous earth, vermiculite, pearlite, attapulgite, white carbon, urea, calcium chloride, ammonium sulfate, sodium sulfate, glucose, sucrose, lactose and paraffin wax, and one or two or more types of so-called thickeners or carriers usually used in agricultural powders or granules can be used in combination.

Examples of liquid carriers which can be used in the composition of the present invention include water, hydrocarbon solvents and solvents other than hydrocarbon solvents.

Examples of binders which can be used in the composition of the present invention include those indicated below. Examples thereof include dextrin, starch, soluble starch, a starch, sodium alginate, gum arabic, tragacanth gum, gelatin, casein, carboxymethyl cellulose sodium, methyl cellulose, ethyl cellulose, hydroxyethyl cellulose, hydroxypropyl cellulose, polyvinyl alcohol, polyacrylamide, sodium polyacrylate, polyethylene glycol, polyvinylpyrrolidone, acrylic acid copolymers and maleic acid copolymers.

Examples of solvents which can be used in the composition of the present invention are indicated below. Examples thereof include alcohols such as ethanol, isopropanol or cyclohexanol; polyvalent alcohols such as ethylene glycol, diethylene glycol, propylene glycol, hexylene glycol, polyethylene glycol or polypropylene glycol; ketones such as cyclohexanone or γ-butyrolactone; esters such as fatty acid methyl esters or dibasic acid methyl esters; nitrogen-containing carriers such as N-alkylpyrrolidones; oils such as palm oil, soybean oil or rapeseed oil; and hydrocarbons such as normal paraffin, naphthene, isoparaffin, xylene, alkyl benzene, alkyl naphthalene or kerosene.

However, these components are not limited to those exemplified above.

The composition of the present invention can be used to control various types of plant diseases. A plant disease as referred to here refers to that in which systemic, abnormal pathological symptoms such as wilting, damping-off, yellowing, dwarfism or spindly growth, or partial pathological symptoms such as spotting, leaf blight, mosaic pattern, leaf rolling, die back, root rot, club root or knotting, are induced by a pathogen in plants such as crops, ornamental plants, ornamental trees and shrubs, or trees, or in other words, that in which a plant becomes ill. Examples of pathogens that cause plant disease mainly include fungi, bacteria, spiroplasmas, phytoplasmas, viruses, viroids, parasitic higher plants and nematodes, and preferable examples of plant diseases include, but are not limited to, plant diseases caused by fungi or bacteria.

Diseases caused by fungi refer to fungal diseases, and fungi account for roughly 80% of pathogens that cause plant diseases. Examples of fungi (pathogens) that cause fungal diseases include Plasmodiophora, Oomycetes, Zygomycetes, Ascomycetes, Basidiomycetes and Deuteromycetes. Examples of Plasmodiophora include, but are not limited to, club root fungus, potato powdery scab fungus and beet necrotic yellow vein virus, examples of Oomycetes include, but are not limited to, blight fungus, downy mildew fungus, *Pythium* species and *Aphanomyces* species, examples of Zygomycetes include, but are not limited to, *Rhizopus* species, examples of Ascomycetes include peach leaf curl fungus, southern corn leaf blight fungus, rice blast fungus, powdery mildew virus, anthracnose fungus, *fusarium* head blight fungus, bakanae fungus and stem rot fungus, examples of Basidiomycetes include, but are not limited to, rust fungus, smut fungus, violet root rot fungus, rice cake disease fungus and rice sheath blight fungus, and examples of Deuteromycetes include, but are not limited to, gray mold fungus, *Alternaria* species, *Fusarium* species, *Penicillium* species, *Rhizoctonia* species and southern blight fungus.

Diseases caused by bacteria refer to bacterial diseases, and bacteria account for roughly 10% of pathogens that cause plant diseases. Examples of bacteria (pathogens) that cause bacterial diseases include members of the phylum Protobacteria, which includes Gram negative bacteria, and members of the phylum Actinobacteria and phylum Firmicutes, which include Gram positive bacteria. Examples of the phylum Proteobacteria include, but are not limited to, α-proteobacteria in the form of *Rhizobium* species and Ca. *Liberibacter* species; β-proteobacteria in the form of *Acidovorax* species, *Burkholderia* species and *Ralstonia* species; γ-proteobacteria in the form of *Pseudomonas* species, *Xanthomonas* species and *Erwinia* species; members of the phylum Actinobacteria in the form of *Streptomyces* species, *Clavibacter* species and *Curtobacterium* species; and members of the phylum Firmicutes in the form of *Bacillus* species and *Clostridium* species.

The composition of the present invention is effective against the following types of plant diseases. Although the following indicates specific diseases and pathogens thereof, the present invention is not limited thereto.

Rice: blast (*Magnaporthe grisea*), sheath blight (*Thanatephorus cucumeris*), brown sclerotial disease (*Ceratobasidium setariae*), small sclerotial disease (*Waitea circinata*), brown sheath blight (*Thanatephorus cucumeris*), globular sclerotial disease (*Sclerotium hydrophilum*), red sclerotial disease (*Wairea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), cercospora leaf spot (*Sphaerulina oryzina*), bakanae disease (*Gibberella fujikuroi*), seedling damping-off (*Pythium* spp., *Fusarium* spp., *Trichoderma* spp., *Rhizopus* spp., *Rhizoctonia solani, Mucor* sp.), seedling rot (*Pythium* spp., *Achlya* spp., *Dictyuchus* spp.), rice false smut (*Claviceps virens*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seeding damping-off (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus);

wheat: powdery mildew (*Blumeria graminis* f. sp. *hordei*, f. sp. *tritici*), rust (*Puccinia striiformis, Puccinia graminis*,

*Puccinia recondite, Puccinia hordei*), leaf blotch (*Pyrenophora graminea*), net blotch (*Pyrenophora teres*), Fusarium head blight (*Gibberella zeae, Fusarium culmorum, Fusarium avenaceum, Monographella nivalis*), Typhula snow blight (*Typhula incarnate, Typhula ishikariensis, Monographella nivalis*), loose kernel smut (*Ustilago nuda*), stinking smut (*Tilletia caries, Tilletia controversa*), eye spot (*Pseudocercosporella herpotrichoides*), foot rot (*Ceratobasidium gramineum*), leaf scald (*Rhynchosporium secalis*), speckled leaf blotch (*Septoria tritici*), glume blotch (*Phaeosphaeria nodorum*), damping-off (*Fusarium* spp., *Pythium* spp., *Rhizoctonia* spp., *Septoria* spp., *Pyrenophora* spp.), seedling blight (*Gaeumannomyces graminis*), anthracnose (*Colletotrichum graminicola*), ergot (*Claviceps purpurea*), leaf spot (*Cochliobolus sativus*), bacterial black node (*Pseudomonas syringae* pv. *syringae*);

corn: leaf rust (*Gibberella zeae*), damping-off (*Fusarium avenaceum, Penicillium* spp. *Pythium* spp., *Rhizoctonia* spp.), rust (*Puccinia sorghi*), brown spot (*Cochliobolus heterostrophus*), loose smut (*Ustilago maydis*), anthracnose (*Colletotrichum graminicola*), northern leaf spot (*Cochliobolus carbonum*), bacterial brown stripe (*Acidovorax avenae* subsp. *avenae*), bacterial stripe (*Burkholderia andropogonis*), bacterial stalk rot (*Erwinia chrysanthemi* pv. *zeae*), bacterial wilt (*Erwinia stewartii*); grapes: downy mildew (*Plasmopara viticola*), rust (*Physopella ampelopsidis*), powdery mildew (*Uncinula necator*), scab (*Elsinoe ampelina*), ripe rot (*Glomerella cingulata, Colletotrichum acutatum*), black rot (*Guignardia bidwellii*), Phomopsis leaf spot (*Phomopsis viticola*), fly speck (*Zygophiala jamaicensis*), gray mold (*Botrytis cinerea*), twig blight (*Diaporthe medusaea*), violet root rot (*Helicobasidium mompa*), white root rot (*Rosellinia necatrix*), crown gall (*Agrobacterium vitis*);

apples: powdery mildew (*Podosphaera leucotricha*), black spot disease (*Venturia inequalis*), Alternaria leaf spot (*Alterneria mali*), rust (*Gymnosporangium yamadae*), blossom blight (*Monilinia mali*), apple canker (*Valla ceratosperma*), ring spot (*Botryosphaeria berengeriana*), anthracnose (*Colletotrichum actutatum, Glomerella cingulata*), fly speck (*Zygophiala jamaicensis*), sooty spot (*Gloeodes pomigena*), fruit spot (*mycosphaerella pomi*), violet root rot (*Helicobasidium mompa*), white root rot (*Rosellinia necatrix*), canker (*Phomopsis mali, Diaporthe tanakae*), apple blotch (*Diplocarpon mali*), fire blight (*Erwinia amylovora*), crown gall (*Agrobacterium tumefaciens*), hairy root disease (*Agrobacterium rhizogenes*); Japanese pears: black spot (*Alternaria kikuchiana*), pear scab (*Venturia nashicola*), rust (*Gymnosporangium asiaticum*), ring spot (*Botryosphaeria berengeriana* f. sp. *piricola*), pear canker (*Phomopsis fukushii*), bacterial shoot blight (*Erwinia* sp.), crown gall (*Agrobacterium tumefaciens*), rusty canker (*Erwinia chrysanthemi* pv. *chrysanthemi*), bacterial petal blight (*Pseudonomas syringae* pv. *syringae*); European pears: blight (*Phytophthora cactorum, Phytophthora syringae*), bacterial shoot blight (*Erwinia* sp.), peaches: black spot (*Cladosporium carpophilum*), Phomopsis rot (*Phomopsis* sp.), blight (*Phytophthora* sp.), anthracnose (*Colletotrichum gloeosporioides*), leaf curl (*Taphrina deformans*), bacterial shot hole (*Xhanthomonas campestris* pv. *pruni*), crown gall (*Agrobacterium tumefaciens*); yellow peaches: anthracnose (*Glomerella cingulata*), young fruit sclerotial disease (*Monilinia kusanoi*), gray spot (*Monilinia fructicola*), crown gall (*Agrobacterium tumefaciens*), bacterial gummosis (*Pseudomonas syringae* pv. *syringae*): persimmons: anthracnose (*Glomerella cingulata*), brown stem rot (*Cercospora kaki, Mycosphaerella nawae*), powdery mildew (*Phyllactinia kakikora*), crown gall (*Agrobacterium tumefaciens*); citrus fruit: melanose (*Diaporthe citri*), green mold disease (*Penicillium digitatum*), blue mold disease (*Penicillium italicum*), scab (*Elsinoe fawcettii*), brown rot (*Phytophthora citrophthora*), canker (*Xhanthomonas campestris* pv. *citri*), bacterial brown spot (*Pseudomonas syringae* pv. *syringae*), greening disease (*Liberibactor asiaticus*), crown gall (*Agrobacterium tumefaciens*);

tomatoes, cucumbers, beans, strawberries, potatoes, cabbage, eggplants, lettuce: gray mold (*Botrytis cinerea*); tomatoes, cucumbers, beans, strawberries, potatoes, rapeseed, cabbage, eggplants, lettuce: sclerotial disease (*Sclerotinia sclerotiorum*); tomatoes, cucumbers, beans, radishes, watermelons, eggplants, rapeseed, green peppers, spinach, beets: seedling damping-off (*Rhizoctonia* spp., *Pythium* spp., *Fusarium* spp., *Phythophthora* spp., *Sclerotinia sclerotiorum*); solanaceous plants: bacterial wilt (*Ralstonia solanacearum*); melons: downy mildew (*Pseudoperonospora cubensis*), powdery mildew (*Sphaerotheca fuliginea*), anthracnose (*Colletotrichum orbiculare*), gummy stem blight (*Didymella bryoniae*), stem rot (*Fusarium oxysporum*), late blight (*Phytophthora parasitica, Phytophthora melonis, Phytophthora nicotianae, Phytophthora drechsleri, Phytophthora capsici*), bacterial brown spot (*Xhanthomonas campestris* pv. *cucurbitae*), soft rot (*Erwinia carotovora* subsp. *carotovora*), bacterial spot (*Pseudomonas syringae* pv. *lachrymans*), marginal blight (*Pseudomonas marginalis* pv. *marginalis*), canker (*Streptomyces* sp.), hairy root disease (*Agrobacterium rhizogenes*), cucumber mosaic virus (Cucumber mosaic virus); tomatoes: ring spot (*Alternaria solani*), leaf mold (*Fulvia fulva*), late blight (*Phytophthora infestans*), wilt disease (*Fusarium oxysporum*), root rot (*Pythium myriotylum, Pythium dissotocum*), anthracnose (*Colletotrichum gloeosporoides*), canker (*Clavibacter michiganensis*), pith necrosis (*Pseudomonas corrugata*), bacterial black spot (*Pseudomonas viridiflava*), soft rot (*Erwinia carotovora* subsp. *carotovora*), bacterial leaf gall (*Crynebacterium* sp.), yellowing wilt (*Phytoplasma asteris*), yellow dwarfism (Tabaco leaf curl, subgroup III geminivirus); eggplants: powdery mildew (*Sphaerotheca fuliginea*), leaf mold (*Mycovellosiella nattrassii*), blight (*Phytophthora infestans*), brown rot (*Phytophthora capsici*), bacterial brown spot (*Pseudomonas cichorii*), necrotic leaf spot (*Pseudomonas corrugata*), bacterial stem rot (*Erwinia chrysanthemi*), soft rot (*Erwinia carotovora* subsp. *carotovora*), bacterial spot (*Pseudomonas* sp.);

Rapeseed: black spot (*Alternaria brassicae*), black rot (*Xhanthomonas campestris* pv. *campestris*), bacterial black spot (*Pseudomonas syringae* pv. *maculicola*), soft rot (*Erwinia carotovora*); cruciferous vegetables: black spot (*Alternaria bassicae*), white spot (*Cercosporella brassicae*), black leg (*Phoma lingam*), club root (Plasmodiophora *brassicae*), downy mildew (*Peronospora parasitica*), black rot (*Xanthomonas campestris* pv. *campestris*), bacterial black spot (*Pseudomonas syringae* pv. *maculicola*), soft rot (*Erwinia carotovora* subsp. *carotovora*); cabbage: club foot (*Thanatephorus cucumeris*), yellowing wilt (*Fusarium oxysporum*); Chinese cabbage: bottom rot (*Rhizoctonia solani*), yellowing (*Verticillium dahliae*); green onions: rust (*Puccinia allii*), black spot (*Alternaria porri*), southern blight (*Sclerotium rolfsii*), white rot (*Phytophthora porri*), black rot (*Sclerotium cepivorum*); onions: canker (*Curtobacterium flaccumfaciens*), soft rot (*Erwinia carotovora* subsp. *carotovora*), bacterial spot (*Pseudomonas syringae* pv. *syringae*), rot (*Erwinia rhapontici*), scale rot (*Burkholderia gladioli*), yellowing wilt (*Phytoplasma asteris*); garlic: soft rot (*Erwinia carotovora* subsp. *carotovora*), spring rot (*Pseudomonas marginalis* pv. *marginalis*); soybeans: purple seed stain (*Cercospora kikuchii*), scab (*Elsinoe glycines*), black spot (*Diaporthe phaseolorum*), Rhizoctonia root rot (*Rhizoctonia solani*), stem rot (*Phytophthora sojae*), downy mildew (*Peronospora manshurica*), rust (*Phakopsora pachyrhizi*), anthracnose (*Colletotrichum truncatum*), leaf scald (*Xhanthomonas campestris* pv. *glycines*), bacterial spot (*Pseudomonas syringae* pv. *glycinea*);

green beans: anthracnose (*Colletotrichum lindemuthianum*), bacterial wilt (*Ralstonia solanacearum*), halo blight (*Pseudomonas syringae* pv. *phaseolicola*), bacterial brown spot (*Pseudomonas viridiflava*), leaf scald (*Xhanthomonas campestris* pv. *phaseoli*); peanuts: leaf spot (*Mycosphaerella berkeleyi*), brown spot (*Mycosphaerella arachidis*), bacterial wilt (*Ralstonia solanacearum*); peas: powdery mildew (*Erysiphe pisi*), downy mildew (*Peronospora pisi*), bacterial stem blight (*Pseudomonas syringae* pv. *pisi*), bacterial stem rot (*Xhanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solanacearum*), black foot disease (*Erwinia carotovora* subsp. *atroseptica*), common scab (*Streptomyces scabies, Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces scabies*), bacterial spot (*Pseudomonas syringae* pv. *aptata*);

carrots: leaf blight (*Alternia dauci*), bacterial gall (*Rhizobacter dauci*), crown gall (*Agrobacterium tumefaciens*), *Streptomyces* scab (*Streptomyces* spp.), soft rot (*Erwinia carotovora* subsp. *carotovora*); strawberries: powdery mildew (*Sphaerotheca aphania* var. *aphanis*), blight (*Phytophthora nicotianae*), anthracnose (*Glomerella cingulata*), fruit rot (*Pythium ultimum*), bacterial wilt (*Ralstonia solanacearum*), angular leaf spot (*Xhanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xhantomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), damping-off (*Ralstonia solanacearum*), Tobacco mosaic virus (Tobacco mosaic virus); cotton: damping-off (*Fusarium oxysporum*); sunflowers: sclerotial disease (*Sclerotinia sclerotiorum*), angular leaf spot (*Xhanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa*), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (*Erwinia carotovora* subsp. *carotovora*), crown gall (*Agrobacterium tumefaciens*), hairy root disease (*Agrobacterium rhizogenes*), chrysanthemum virescence (*Phytoplasma aurantifolia*); grasses: brown patch disease (*Rhizoctonia solani*), dollar spot disease (*Sclerotinia homoeocarpa*), curvularia leaf blight (*Curvularia* sp.), rust (*Puccinia zoysiae*), helminthosporium leaf blight (*Cochliobolus* sp.), scald (*Rhynchosporum secalis*), damping-off (*Gaeumannomyces graminis*), anthracnose (*Colletotrichum* sp.), typhula brown snow blight (*Typhula incarnata*), typhula black snow blight (*Typhula ishikariensis*), Sclerotinia (*Myriosclerotina borealis*), fairy ring disease (*Marasmius oreades*), Pythium blight (*Pythium aphanidermatum*), blast (*Pyricularia grisea*).

Although the method to apply the composition of the present invention comprises contacting the composition with a plant body or seeds, or contacting the composition with the roots or underground stem of a plant by containing in cultivation soil, and specific examples thereof include treatment such as spraying the composition onto the stem and leaves of a plant individual, treating seedling nursery boxes, treating by spraying onto the surface of soil, mixing into the soil after treating by spraying onto the surface of soil, soil injection treatment, mixing into the soil after soil injection treatment, soil irrigation treatment, mixing into the soil after soil irrigation treatment, treating by spraying plant seeds, plant seed coating treatment, plant seed immersion treatment and plant seed powder coating treatment, the composition demonstrates adequate effects when applied by any method usually used by a person with ordinary skill in the art.

Namely, the present invention relates to a method for controlling plant disease by applying the composition to a plant body; said method wherein the application to the plant body comprises contacting the composition with a plant body or seeds, or contacting the composition with the roots or underground stem of a plant by containing in cultivation soil; said method in which the application to cultivation soil comprises treating the surface of soil with the composition, irrigating the soil with the composition, or mixing the composition into soil.

Although the applied amount and applied concentration of the composition of the present invention varies according to the target crop, target disease, degree of progression of the disease, formulation of the compound, application method and various environmental conditions and the like, in the case of spraying or irrigation, the applied amount as the amount of active ingredient (monosaccharide) is suitably 50 g to 1,000,000 g per hectare and preferably 100 g to 500,000 g per hectare. In addition, the amount in the case of seed treatment as the amount of active ingredient (monosaccharide) is 0.001 g to 50 g and preferably 0.01 g to 10 g per kg of seeds. In the case of applying the composition of the present invention to a plant individual by stem and leaf spraying treatment, soil surface spraying treatment, soil injection treatment or soil irrigation treatment, treatment may be carried out after having diluted to a suitable concentration in a suitable carrier. In the case of contacting the composition of the present invention with seeds, the seeds may be subjected to immersion, powder coating, spraying or coating treatment on plant seeds after having diluted to a suitable concentration. Although the amount of the composition in the case of powder coating, spraying or coating treatment as the amount of the active ingredient (monosaccharide) is usually about 0.05% to 50% and more preferably 0.1% to 30% based on the dry weight of the plant seeds, the amount is not limited to these ranges, but rather can be altered according to the form of the composition and type of plant seeds targeted for treatment.

A "plant body" as referred to in the present invention refers to that which thrives by photosynthesis without moving. More specifically, examples thereof include, but are not limited to, agricultural and horticultural crops such as rice, wheat, barley, corn, grapes, apples, pears, peaches, yellow peaches, persimmons, citrus fruit, soybeans, green beans, strawberries, potatoes, cabbage, lettuce, tomatoes, cucumbers, eggplants, watermelons, beets, spinach, peas, squash, sugar cane, tobacco, green peppers, sweet potatoes, taro potatoes, konjak, cotton, sunflowers, tulips, chrysanthemums or grasses. In addition, a "plant body" as referred to in the present invention also refers to the generic term for all sites that compose the aforementioned plant individual, and examples thereof include the stems, leaves, roots, seeds, flowers and fruit.

A "seed" as referred to in the present invention refers to that which is used for agricultural production by storing nutrients for the germination of seedlings. Specific examples thereof include, but are not limited to, seeds of corn, soybeans, cotton, rice, beets, wheat, barley, sunflowers, tomatoes, cucumbers, eggplants, spinach, peas, squash, sugar cane, tobacco, green peppers and rape, seed tubers of taro potatoes, potatoes, sweet potatoes and konjak, bulbs of edible lilies and tulips, seed bulbs of scallions, and gene recombinant crops that are plants created by genetic or other artificial manipulation that are inherently not present in nature, examples of which include, but are not limited to, soybeans, corn or cotton that has been imparted with resistance to herbicides, rice or tobacco acclimated to cold climates, corn or cotton seeds that have been imparted with the ability to produce insecticidal substances, and potato tubers.

The composition of the present invention can be mixed or used in combination with other agricultural chemicals as necessary, examples of which include agricultural chemicals, soil improvers and fertilizing substances such as fungicides, insecticides, miticides, nematicides, herbicides or plant growth regulators.

In the present invention, in addition to using a composition comprising a monosaccharide and assistant as previously described, a composition comprising a monosaccharide as active ingredient and a composition comprising the aforementioned assistant can be also be used simultaneously or separately. In the case of using separately, after having first used a composition containing a monosaccharide as active ingredient or a composition containing the aforementioned assistant, the other composition may be used, and which composition is used first is arbitrary. Namely, the present invention also relates to a method for enhancing the control effects of a monosaccharide on a plant disease, comprising applying, either simultaneously or separately, to a plant body a monosaccharide and at least one or more selected from a nonionic surfactant (excluding acetylene glycol-based surfactants, fluorine-based surfactants and silicone-based surfactants), an anionic surfactant (excluding lignin sulfonate), a cationic surfactant, an amphoteric surfactant, a water-soluble polymer, an amino acid, an amino sugar, a disaccharide alcohol and a salt.

Details regarding the composition of the present invention are explained in the examples and test examples. However, the present invention is not limited in any way by these examples and test examples.

Furthermore, in the following test examples, HLB refers to a value that represents the degree of affinity of a surfactant to water and oil. The HLB value can adopt a value from 0 to 20, and the closer the value is to zero, the higher the lipophilicity of that surfactant, while the closer the value is to 20, the higher the hydrophilicity of that surfactant. In addition, "nt" stands for "not tested".

In addition, in the following examples and test examples, "parts" represents "parts by weight".

EXAMPLES

[Example 1] Trial Production of Water-Soluble Powders 80 parts of D-tagatose and 20 parts of Neopelex No. 6F Powder (aryl sulfonate, Kao Corp.) were mixed followed by crushing with a hammer mill to obtain the composition of the present invention in the form of a water-soluble powder. In addition, the composition of the present invention in the form of a water-soluble powder was obtained using the same production method while replacing Neopelex No. 6F Powder component with Newcol 2614 (polyoxyalkylene aryl ether, Nippon Nyukazai Co., Ltd.) or Amycol No. 1 (dextrin, Nippon Starch Chemical Co., Ltd.), and these were used in Test Example 1.

[Example 2] Trial Production of Liquid Preparations 4 parts of D-tagatose, 1 part of Neopelex No. 6F Powder and 95 parts of water were added, mixed and dissolved to obtain the composition of the present invention in the form of a liquid preparation. In addition, the composition of the present invention was obtained in the form of a liquid preparation using the same production method while replacing Neopelex 6F Powder component with Newcol 2614, Acetamin 24 (alkyl amine salt, Kao Corp.), Amphitol 24B (alkyl betaine, Kao Corp.), or Amycol No. 1, and these were used in Test Example 2.

[Example 3] Trial Production of Water-Soluble Granules (Extrusion Granulation)

80 parts of D-tagatose and 20 parts of Neopelex No. 6F Powder were mixed followed by adding 2 parts of water and kneading. Next, this hydrated mixture was granulated with an extrusion granulator equipped with a screen having a hole size of 1.0 mm. After drying the resulting granules with a fluidized bed dryer, the granules were passed through a sieve having an opening size of 500 μm to 1410 μm to obtain the composition of the present invention in the form of water-soluble granules. In addition, the composition of the present invention was obtained in the form of water-soluble granules using the same production method while replacing Neopelex No. 6F Powder with Amycol No. 1, and these were used in Test Example 3.

[Example 4] Trial Production of Water-Soluble Granules (Agitation Granulation)

80 parts of D-tagatose and 20 parts of Neopelex No. 6F Powder were mixed followed by adding 2 parts of water and subjecting to agitation granulation. Next, after drying the resulting granules with a shelf dryer, the granules were passed through a sieve having an opening size of 500 μm to 2000 μm to obtain the composition of the present invention in the form of water-soluble granules. In addition, the composition of the present invention was obtained in the form of water-soluble granules using the same production method while replacing Neopelex No. 6F Powder with Amycol No. 1, and these were used in Test Example 4.

[Example 5] Trial Production of Water-Soluble Powders Comprising Nonionic Surfactant Compositions of the present invention in the form of water-soluble powders were obtained using the same production method as Example 1 while replacing Neopelex No. 6F Powder component of Example 1 with various types of nonionic surfactants, and these were used in Test Example 5.

[Example 6] Trial Production of Water-Soluble Powders Comprising Anionic, Cationic or Amphoteric Surfactant Compositions of the present invention in the form of water-soluble powders were obtained using the same production method as Example 1 while replacing Neopelex No. 6F Powder component of Example 1 with various types of anionic surfactants, cationic surfactants or amphoteric surfactants, and these were used in Test Example 6.

[Example 7] Trial Production of Water-Soluble Powders Comprising Water-Soluble Polymer Compositions of the present invention were obtained in the form of water-soluble powders using the same production method as Example 1 while replacing Neopelex No. 6F Powder component of Example 1 with various types of water-soluble polymers, and these were used in Test Example 7.

[Example 8] Trial Production of Liquid Preparations Comprising Amino Acid, Amino Sugar or Disaccharide Alcohol 5 parts of D-tagatose, 5 parts of isomalt (palatinit) and 90 parts of water were added, mixed and dissolved to obtain the composition of the present invention in the form of a liquid preparation. In addition, compositions of the present invention were obtained in the form of liquid preparations using the same production method while replacing the isomalt with various types of sugars, including disaccharide alcohols and amino sugars, or amino acids, nucleic acid bases, nucleosides or organic acids, and these were used in Test Example 8.

[Example 9] Trial Production of Liquid Preparations Comprising Various Types of Monosaccharides Other than D-Tagatose and Various Types of Anionic Surfactants 10 parts of D-psicose, D-sorbose, D-allose, D-talose, D-galactose, L-fructose or D-mannose, 0.25 to 0.5 parts of various types of anionic surfactants, and 89.5 to 89.75 parts of water were added, mixed and dissolved to obtain compositions of the present invention in the form of liquid preparations, and these were used in Test Example 9.

[Example 10] Trial Production of Water-Soluble Powders Comprising Multiple Types of Surfactants 80 parts of D-tagatose, 7.5 to 19 parts of a mixture of multiple types of anionic surfactants and 1 to 12.5 parts of lactose were mixed followed by crushing with a hammer mill to obtain compositions of the present invention in the form of water-soluble powders (Formulas 1 to 11). In addition, 7.5 to 19 parts of various types of anionic surfactants were mixed with 81 to 92.5 parts of lactose followed by crushing with a hammer mill to obtain compositions of the present invention in the form of water-soluble powders (Formulas 12 to 22). In addition, compositions of the present invention in the form of water-soluble powders were obtained by crushing only D-tagatose with a hammer mill (Formulas 23 and 24). These compositions were used in Test Example 10.

[Example 11] Trial Production of Water-Soluble Powders Comprising Anionic Surfactant 80 parts of D-tagatose and 20 parts of various types of anionic surfactants were mixed, 80 parts of lactose and 20 parts of various types of anionic surfactants were mixed in the case of not incorporating a main agent, or 80 parts of D-tagatose and 20 parts of lactose were mixed in the case of D-tagatose only, followed by crushing with a hammer mill to obtain water-soluble powders of the composition of the present invention, and these were used in Test Example 11.

[Example 12] Trial Production of Liquid Preparations Comprising Sugars, Amino Acids, Salts and Anionic Surfactants 5 parts of D-tagatose, 5 parts of various types of sugars and 90 parts of water were added and mixed to obtain compositions of the present invention in the form of liquid preparations (Main Agent+Assistant 1). In addition, 5 parts of D-tagatose, 5 parts of various types of sugars, anionic surfactant in the form of 0.016 parts of alkyl benzene sulfonate, 0.3 parts of alkyl sulfate or 0.3 parts of alkyl naphthalene sulfonate and 89 parts of water were added and mixed to obtain compositions of the present invention in the form of liquid preparations (Main Agent+Assistant 1+Assistant 2). In addition, compositions of the present invention in the form of liquid preparations were obtained using the same production method while replacing the sugar with an amino acid or salt, and these were used in Test Example 12.

In addition, 5 parts of D-tagatose and 95 parts of water in the case of a main agent only, 5 parts of D-tagatose and an anionic surfactant in the form of 0.016 parts of alkyl benzene sulfonate, 0.3 parts of alkyl sulfate or 0.3 parts of alkyl naphthalene sulfonate and 94 parts of water in the case of only a main agent and anionic surfactant, or 0.016 parts of alkyl benzene sulfonate, 0.3 parts of alkyl sulfate or 0.3 parts of alkyl naphthalene sulfonate and 99 parts of water in the case of anionic surfactant only, were mixed to obtain compositions of the present invention in the form of liquid preparations, and these were used in Test Example 12.

[Example 13] Trial Production of Water-Soluble Powders Comprising Various Types of Sugars and Anionic Surfactants 20 to 80 parts of D-tagatose and 2.5 to 30 parts of D-glucose, D-fructose, D-galactose, D-mannose, D-talose, D-sorbose, D-psicose or lactose were added and mixed followed by crushing with a hammer mill to obtain compositions of the present invention in the form of water-soluble powders (Compound 1+Compound 2+Compound 3). In addition, 20 to 80 parts of D-tagatose, 2.5 to 30 parts of D-glucose, D-fructose, D-galactose, D-mannose, D-talose, D-sorbose, D-psicose or lactose, and anionic surfactant in the form of 0.25 parts of alkyl benzene sulfonate, 5 parts of alkyl sulfate or 5 parts of alkyl naphthalene sulfonate were added and mixed followed by crushing with a hammer mill to obtain compositions of the present invention in the form of water-soluble powders (Compound 1+Compound 2+Compound 3+Assistant). In addition, 0.25 to 5 parts of various types of anionic surfactants and 90 parts of lactose were mixed followed by crushing with a hammer mill to obtain compositions of the present invention in the form of water-soluble powders (assistant only). These compositions were used in Test Example 13.

Evaluation of Compositions of Present Invention
([Test Examples 1 to 10, 12 and 13])

In the present test examples, control tests were carried out on cucumber downy mildew (CDM), grape vine downy mildew (VDM), cucumber powdery mildew (CPM), wheat brown rust (WR), tomato late blight (LB), barley powdery mildew (BPM), grape vine rust (VR), soybean rust (SR), tomato gray mold (GM), rice blast (B), cucumber anthracnose (CA), apple scab (AS), wheat *septoria* leaf blotch (SLB), rice sheath blight (SB), cucumber bacterial spot (CBS), Chinese cabbage soft rot (CSR) and tomato bacterial wilt (TBW). Details of the test methods are indicated below.

(CDM: Cucumber Downy Mildew)

Test plants (cucumber variety: Sagami Hanjiro) were planted followed by cultivating until the first leaf appeared. In the test, dilutions (5 ml/pot) obtained by diluting with distilled water so that each formula reached a prescribed concentration were sprayed. After inoculating the seedlings one day after spraying by spraying with $1 \times 10^3$ organisms/ml of a sporangium suspension of *Pseudoperonospora cubensis*, the seedlings were allowed to stand for about 24 hours in an inoculation room at a room temperature of 20° C. to promote the onset of disease. Disease development was investigated 7 days after inoculation, and the effects thereof were evaluated.

(VDM: Vine Downy Mildew)

Test plants (grape variety: Neomuscat) were planted followed by cultivating until three to four first leaves appeared. In the test, dilutions (5 ml/pot) obtained by diluting with distilled water so that each formula reached a prescribed concentration were sprayed. After inoculating the seedlings one day after spraying by spraying with $1 \times 10^3$ organisms/ml of a sporangium suspension of *Plasmopara viticola*, the seedlings were allowed to stand for about 24 hours in an inoculation room at a room temperature of 20° C. to promote the onset of disease. Disease development was investigated 10 days after inoculation, and the effects thereof were evaluated.

(CPM: Cucumber Powdery Mildew)

Test plants (cucumber variety: Sagami Hanjiro) were planted followed by cultivating until one first leaf appeared. In the test, dilutions (5 ml/pot) obtained by diluting with distilled water so that each formula reached a prescribed concentration were sprayed. After inoculating the seedlings one day after spraying by spraying with $1 \times 10^7$ organisms/ml of conidia of *Sphaerotheca cucurbitae*, disease development was investigated 7 days after, and the effects thereof were evaluated.

(WR: Wheat Brown Rust)

Test plants (wheat variety: Norin 61) were planted followed by cultivating until the second leaf appeared. In the test, dilutions (5 ml/pot) obtained by diluting with distilled water so that each formula reached a prescribed concentration were sprayed. After inoculating the seedlings one day after spraying by spraying with $1 \times 10^7$ organisms/ml of uredospores of *Puccinia recondita*, disease development was investigated 10 days after, and the effects thereof were evaluated.

(LB: Tomato Late Blight)

Test plants (tomato variety: Oogata Fukuju) were planted followed by cultivating until five first leaves appeared. In the test, dilutions (5 ml/pot) obtained by diluting with distilled water so that each formula reached a prescribed concentration were sprayed. After inoculating the seedlings one day after spraying by spraying with $1 \times 10^3$ organisms/ml of a sporangium suspension of *Phytophthora infestans*, the seedlings were allowed to stand for about 24 hours in an inoculation room at a room temperature of 20° C. to promote the onset of disease. Disease development was investigated 7 days after inoculation, and the effects thereof were evaluated.

(BPM: Barley Powdery Mildew)

Test plants (barley variety: Sekishinryoku) were planted followed by cultivating until the second leaf appeared. In the test, dilutions (5 ml/pot) obtained by diluting with distilled water so that each formula reached a prescribed concentration were sprayed. After inoculating the seedlings one day after spraying by shaking off conidia of *Blumeria graminis* f sp. *hordei* onto the seedlings, disease development was investigated 7 days after, and the effects thereof were evaluated.

(VR: Vine Rust)

Test plants (grape variety: Neomuscat) were planted followed by cultivating until three to four first leaves appeared. In the test, dilutions (5 ml/pot) obtained by diluting with distilled water so that each formula reached a prescribed concentration were sprayed. After inoculating the seedlings one day after spraying by spraying with $1 \times 10^7$ organisms/ml of uredospores of *Phakopsora ampelopsidis*, the seedlings were allowed to stand for about 24 hours in an inoculation room at a room temperature of 20° C. to 23° C. to promote the onset of disease. Disease development was investigated 12 days after inoculation, and the effects thereof were evaluated.

(SR: Soybean Rust)

Test plants (soybean variety: Enrei) were planted followed by cultivating until two first leaves appeared. In the test, dilutions (5 ml/pot) obtained by diluting with distilled water so that each formula reached a prescribed concentration were sprayed. After inoculating the seedlings one day after spraying by spraying with $1 \times 10^7$ organisms/ml of uredospores of *Phakopsora pachyrhizi*, the seedlings were allowed to stand for about 24 hours in an inoculation room at a room temperature of 20° C. to 23° C. to promote the onset of disease. Disease development was investigated 12 days after inoculation, and the effects thereof were evaluated.

(GM: Gray Mold)

Test plants (tomato variety: Oogata Fukuju) were planted followed by cultivating until three first leaves appeared. In the test, dilutions (5 ml/pot) obtained by diluting with distilled water so that each formula reached a prescribed concentration were sprayed. After inoculating the seedlings one day after spraying by spraying with $1 \times 10^7$ organisms/ml of conidia of *Botrytis cinerea*, the seedlings were allowed to stand for about 48 hours in an inoculation room at a room temperature of 20° C. to 23° C. to promote the onset of disease. Disease development was investigated 2 days after inoculation, and the effects thereof were evaluated.

(B: Blast)

Test plants (rice variety: Sachikaze) were planted followed by cultivating until the second leaf appeared. In the test, dilutions (5 ml/pot) obtained by diluting with distilled water so that each formula reached a prescribed concentration were sprayed. After inoculating the seedlings one day after spraying by spraying with 1×10$^5$ organisms/ml of conidia of *Magnaporthe grisea*, the seedlings were allowed to stand for about 24 hours in an inoculation room at a room temperature of 20° C. to 23° C. to promote the onset of disease. Disease development was investigated 10 days after inoculation, and the effects thereof were evaluated.

(CA: Cucumber Anthracnose)

Test plants (cucumber variety: Sagami Hanjiro) were planted followed by cultivating until the first leaf appeared. In the test, dilutions (5 ml/pot) obtained by diluting with distilled water so that each formula reached a prescribed concentration were sprayed. After inoculating the seedlings one day after spraying by spraying with $1\times10^7$ organisms/ml of conidia of *Colletotrichum orbiculare*, the seedlings were allowed to stand for about 24 hours in an inoculation room at a room temperature of 20° C. to 23° C. to promote the onset of disease. Disease development was investigated 10 days after inoculation, and the effects thereof were evaluated.

(AS: Apple Scab)

Test plants (apple variety: Ohrin) were planted followed by cultivating until four first leaves appeared. In the test, dilutions (5 ml/pot) obtained by diluting with distilled water so that each formula reached a prescribed concentration were sprayed. After inoculating the seedlings one day after spraying by spraying with $1\times10^5$ organisms/ml of conidia of *Venturia inaequalis*, the seedlings were allowed to stand for about 24 hours in an inoculation room at a room temperature of 18° C. to 20° C. to promote the onset of disease. Disease development was investigated 10 days after inoculation, and the effects thereof were evaluated.

(SLB: *Septoria* Leaf Blotch)

Test plants (wheat variety: Norin 61) were planted followed by cultivating until the second leaf appeared. In the test, dilutions (5 ml/pot) obtained by diluting with distilled water so that each formula reached a prescribed concentration were sprayed. After inoculating the seedlings one day after spraying by spraying with $1\times10^7$ organisms/ml of conidia of *Septoria tritici*, the seedlings were allowed to stand for about 24 hours in an inoculation room at a room temperature of 18° C. to promote the onset of disease. Disease development was investigated 14 days after inoculation, and the effects thereof were evaluated.

(SB: Sheath Blight)

Test plants (rice variety: Sachikaze) were planted followed by cultivating until the third leaf appeared. In the test, dilutions (5 ml/pot) obtained by diluting with distilled water so that each formula reached a prescribed concentration were sprayed. After inoculating the seedlings one day after spraying with clumps of *Rhizoctonia solani* AGI-IA cultured for 14 days in oat medium, the seedlings were allowed to stand for about 24 hours in an inoculation room at a room temperature of 28° C. to promote the onset of disease. Disease development was investigated 14 days after inoculation, and the effects thereof were evaluated.

(CBS: Cucumber Bacterial Spot)

Test plants (cucumber variety: Sagami Hanjiro) were planted followed by cultivating until the first leaf appeared. In the test, dilutions (5 ml/pot) obtained by diluting with distilled water so that each formula reached a prescribed concentration were sprayed. After inoculating the seedlings one day after spraying by spraying with $1\times10^6$ organisms/ml of *Pseudomonas syringae* pv. *lachrymans*, the seedlings were allowed to stand for about 24 hours in an inoculation room at a room temperature of 25° C. to promote the onset of disease. Disease development was investigated 10 days after inoculation, and the effects thereof were evaluated.

(CSR: Cabbage Soft Rot)

Test plants (cabbage variety: Muso) were planted followed by cultivating until two first leaves appeared. In the test, dilutions (5 ml/pot) obtained by diluting with distilled water so that each formula reached a prescribed concentration were sprayed. After wound-inoculating the seedlings one day after spraying with $1\times10^5$ organisms/ml of *Erwinia carotovora* subsp. *carotovora*, the seedlings were allowed to stand for about 24 hours in an inoculation room at a room temperature of 23° C. to promote the onset of disease. Disease development was investigated 1 day after inoculation, and the effects thereof were evaluated.

(TBW: Tomato Bacterial Wilt)

Test plants (tomato variety: Oogata Fukuju) were planted followed by cultivating until three first leaves appeared. In the test, dilutions (5 ml/pot) obtained by diluting with distilled water so that each formula reached a prescribed concentration were sprayed. After wound-inoculating the seedlings one day after spraying with $1\times10^5$ organisms/ml of *Ralstonia solanacearum*, the seedlings were allowed to stand for about 24 hours in an inoculation room at a room temperature of 25° C. to promote the onset of disease. Disease development was investigated 10 days after inoculation, and the effects thereof were evaluated.

Disease development was evaluated using the following indicators for disease control tests evaluated according to the methods described above. Furthermore, preventive values were calculated based on the disease development.

[Disease Development]

0: No onset of disease
0.1: Diseased area of about 3%
0.3: Diseased area of about 10%
0.8: Diseased area of about 25%
1.5: Diseased area of about 50%
2: Diseased area of about 70%
3: Diseased area of 95% or more

[Preventive Value]

Preventive value=100 {1−(n/N)}
N=Disease development of untreated group
n=Disease development of each group

[Test Example 1] Evaluation of Compositions (Water-Soluble Powders)

The effects of the D-tagatose water-soluble powders prepared in Example 1 on cucumber downy mildew were evaluated. Moreover, the degree of improvement in preventive value attributable to the formulas of the present invention with respect to a formula containing D-tagatose only was evaluated using the following indices as indicators. Furthermore, the improvement in efficacy with respect to cucumber downy mildew was evaluated based on the control effect of a 200-fold dilution (treatment concentrations: D-tagatose 0.4%+assistant 0.1%). Those results are shown in Table 1.

0: Equal or decrease in preventive value in comparison with formula containing T-tagatose only
1: Improvement in preventive value of 1 to less than 10
2: Improvement in preventive value of 10 to less than 20
3: Improvement in preventive value of 20 to less than 30
4: Improvement in preventive value of 30 to less than 40
5: Improvement in preventive value of 40 or more Furthermore, the preventive value of the formula containing D-tagatose only with respect to cucumber downy mildew at a treatment concentration of 0.4% was about 50 (40 to 60).

A remarkable improvement in control effect against cucumber downy mildew was observed with water-soluble powders containing anionic surfactant, nonionic surfactant or water-soluble polymer with respect to the formula containing D-tagatose only.

TABLE 1

Test Example 1: Water-Soluble Powders

| Broad Classification | Intermediate Classification | Narrow Classification | Product Name | Supplier | D-tagatose Content (parts) | Assistant Content (parts) | Evaluation Score CDM |
|---|---|---|---|---|---|---|---|
| Anionic surfactant | Aryl sulfonate | Alkyl benzene sulfonate | Neopelex No. 6F | Kao Corp. | 80 | 20 | 5 |
| Nonionic surfactant | Polyoxyalkylene aryl ether | Polyoxyethylene styryl phenyl ether | Newcol 2614 | Nippon Nyukazai Co., Ltd. | 80 | 20 | 5 |
| Water-soluble polymer | Modified starch | Dextrin | Amycol No. 1 | Nippon Starch Chemical Co., Ltd. | 80 | 20 | 5 |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

[Test Example 2] Evaluation of Compositions (Liquid Preparations)

The effects of the D-tagatose liquid preparations prepared in Example 2 against cucumber downy mildew were evaluated using the same test method and evaluation method as Test Example 1. Moreover, the degree of improvement in preventive value attributable to the formulas of the present invention with respect to a formula containing D-tagatose only was evaluated using the same indices as Test Example 1 as indicators. The improvement in efficacy with respect to cucumber downy mildew was evaluated based on the control effect of a 10-fold dilution (treatment concentrations: D-tagatose 0.4%+assistant 0.1%). Those results are shown in Table 2.

A remarkable improvement in control effect against cucumber downy mildew was observed with liquid preparations containing anionic surfactant, nonionic surfactant, cationic surfactant, amphoteric surfactant or water-soluble polymer with respect to the formula containing D-tagatose only.

TABLE 2

Test Example 2: Liquid Preparations

| Broad Classification | Intermediate Classification | Narrow Classification | Product Name | Supplier | D-tagatose Content (parts) | Assistant Content (parts) | Water Content (parts) | Evaluation Score CDM |
|---|---|---|---|---|---|---|---|---|
| Anionic surfactant | Aryl sulfonate | Alkyl benzene sulfonate | Neopelex No. 6F | Kao Corp. | 4 | 1 | 95 | 5 |
| Nonionic surfactant | Polyoxyalkylene aryl ether | Polyoxyethylene styryl phenyl ether | Newcol 2614 | Nippon Nyukazai Co., Ltd. | 4 | 1 | 95 | 5 |
| Cationic surfactant | Alkyl amine salt | Coconut amine acetate | Acetamin 24 | Kao Corp. | 4 | 1 | 95 | 5 |
| Amphoteric surfactant | Alkyl betaine | Lauryl betaine | Amphitol 246 | Kao Corp. | 4 | 1 | 95 | 4 |
| Water-soluble polymer | Modified starch | Dextrin | Amycol No. 1 | Nippon Starch Chemical Co., Ltd. | 4 | 1 | 95 | 5 |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

[Test Example 3] Evaluation of Compositions (Water-Soluble Granules (Extrusion Granulation))

The effects of the D-tagatose water-soluble granules prepared in Example 3 against cucumber downy mildew were evaluated using the same test method and evaluation method as Test Example 1 (200-fold dilution, treatment concentrations: D-tagatose 0.4%+assistant 0.1%). Moreover, the degree of improvement in preventive value attributable to the formulas of the present invention with respect to a formula containing D-tagatose only was evaluated using the same indices as Test Example 1 as indicators. Those results are shown in Table 3.

A remarkable improvement in control effect against cucumber downy mildew was observed with water-soluble granules containing anionic surfactant or water-soluble polymer with respect to the formula containing D-tagatose only.

TABLE 3

Test Example 3: Water-Soluble Granules (Extrusion Granulation)

| Broad Classification | Intermediate Classification | Narrow Classification | Product Name | Supplier | D-tagatose Content (parts) | Assistant Content (parts) | Evaluation Score CDM |
|---|---|---|---|---|---|---|---|
| Anionic surfactant | Aryl sulfonate | Alkyl benzene sulfonate | Neopelex No. 6F | Kao Corp. | 80 | 20 | 5 |
| Water-soluble polymer | Modified starch | Dextrin | Amycol No. 1 | Nippon Starch Chemical Co., Ltd. | 80 | 20 | 5 |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

[Test Example 4] Evaluation of Compositions (Water-Soluble Granules (Agitation Granulation))

The effects of the D-tagatose water-soluble granules prepared in Example 4 against cucumber downy mildew were evaluated using the same test method and evaluation method as Test Example 1 (200-fold dilution, treatment concentrations: D-tagatose 0.4%+assistant 0.1%). Moreover, the degree of improvement in preventive value attributable to the formulas of the present invention with respect to a formula containing D-tagatose only was evaluated using the same indices as Test Example 1 as indicators. Those results are shown in Table 4.

A remarkable improvement in control effect against cucumber downy mildew was observed with water-soluble granules containing anionic surfactant or water-soluble polymer with respect to the formula containing D-tagatose only.

cucumber downy mildew was evaluated based on the control effect of a 200-fold dilution (treatment concentrations: D-tagatose 0.4%+assistant 0.1%), while the improvement in efficacy with respect to other diseases was evaluated based on the control effect of a 100-fold dilution (treatment concentrations: D-tagatose 0.8%, assistant: 0.2%). Those results are shown in Table 5.

The preventive value of the formula containing D-tagatose only with respect to cucumber downy mildew at a treatment concentration of 0.4% was about 50 (40 to 60), the preventive value with respect to grave vine downy mildew at a treatment concentration of 0.8% was about 40 (30 to 50), the preventive value with respect to cucumber powdery mildew at a treatment concentration of 0.8% was about 50 (40 to 60), and the preventive value with respect to wheat rash at a treatment concentration of 0.8% was about 5 (0 to 10).

TABLE 4

Test Example 4: Water-Soluble Granules (Agitation Granulation)

| Broad Classification | Intermediate Classification | Narrow Classification | Product Name | Supplier | D-tagatose Content (parts) | Assistant Content (parts) | Evaluation Score CDM |
|---|---|---|---|---|---|---|---|
| Anionic surfactant | Aryl sulfonate | Alkyl benzene sulfonate | Neopelex No. 6F | Rhondia Nicca Ltd. | 80 | 20 | 5 |
| Water-soluble polymer | Modified starch | Dextrin | Amycol No. 1 | Nippon Starch Chemical Co., Ltd. | 80 | 20 | 5 |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

[Test Example 5] Evaluation of Compositions Containing Nonionic Surfactant (Water-Soluble Powder)

The effects of the D-tagatose water-soluble powders containing nonionic surfactant prepared in Example 5 against cucumber downy mildew, grape vine downy mildew, cucumber powdery mildew and wheat rust were evaluated using the same test method and evaluation method as Test Example 1. Moreover, the degree of improvement in preventive value attributable to the formulas of the present invention with respect to a formula containing D-tagatose only was evaluated using the same indices as Test Example 1 as indicators. The improvement in efficacy with respect to Remarkable improvements in control effects against cucumber downy mildew, grave vine downy mildew, cucumber powdery mildew and wheat rust were observed with formulas containing as assistants nonionic surfactants selected from polyoxyalkylene alkyl ethers, polyoxyalkylene alkyl amines, alkyl polyglycosides, polyoxyalkylene aryl ethers, glycerin fatty acid esters, polyglycerin fatty acid esters, propylene glycol fatty acid esters, sorbitan fatty acid esters, polyoxyethylene sorbitan fatty acid esters, fatty acid diethanolamines and alkyl imidazolinones with respect to the formula containing only D-tagatose as monosaccharide. On the other hand, remarkable improvements in control effects were not observed with formulas containing fluorine-based surfactants, silicone-based surfactants or acetylene glycol-based surfactants.

TABLE 5

Test Example 5: Nonionic Surfactants

| Broad Classification | Intermediate Classification | Narrow Classification | Product Name | Supplier | HLB | Assistant Content (parts) | CDM | VDM | CPM | WR |
|---|---|---|---|---|---|---|---|---|---|---|
| Norionic surfactant | Polyoxyalkylene alkyl ether | Polyoxyethylene alkyl ether | (POE $C_{12}C_{12}$ alcohol ether) Newcol 2320 | Nippon Nyukazai Co., Ltd. | 16.4 | 20 | 5 | 5 | 1 | 5 |
| | | | (POE sec-alcohol ether) Newcol NT-5 | Nippon Nyukazai Co., Ltd. | 10.5 | 20 | 5 | 4 | 5 | 5 |
| | | | (POE sec-alcohol ether) Newcol NT-12 | Nippon Nyukazai Co., Ltd. | 14.5 | 20 | 5 | 4 | 5 | 5 |
| | | | (POE castor oil ether) Newcol 1525 | Nippon Nyukazai Co., Ltd. | 10.5 | 20 | 5 | 4 | 2 | 5 |
| | | | (POE castor oil ether) Newcol 1545 | Nippon Nyukazai Co., Ltd. | 13.8 | 20 | 3 | 3 | 2 | 3 |
| | | | (POE hydrogenated castor oil ether) New Kalgen D-220K | Takemoto OI & Fat Co., Ltd. | 10.1 | 20 | 3 | 4 | 4 | 5 |
| | | | (POE hydrogenated castor oil ether) New Kalgen D-240K | Takemoto OI & Fat Co., Ltd. | 13.3 | 20 | 1 | 4 | 4 | 4 |
| | | Polyoxyalkylene alkyl ether | (POA $C_{12}C_{13}$ alcohol ether) Newcol 2304-Y | Nippon Nyukazai Co., Ltd. | 9.3 | 20 | 5 | 4 | 5 | 5 |
| | | | (POA $C_{12}C_{13}$ alcohol ether) Newcol 2308-Y | Nippon Nyukazai Co., Ltd. | 14.7 | 20 | 5 | 4 | 5 | 5 |
| | | | (POA $C_{12}C_{13}$ alcohol ether) Newcol 2314-Y | Nippon Nyukazai Co., Ltd. | 19.0 | 20 | 4 | 3 | 5 | 4 |
| | Polyoxyalkylene alkyl amine | Polyoxyethylene alkyl amine | (POE alkyl (beef tallow) amine) Ethomeen T/15 | Lion Akzo Co., Ltd. | 9.1 | 20 | 1 | 5 | 1 | 4 |
| | | Polyoxyalkylene alkyl amine | Tonet EP-3000S | Sanyo Chemical Industries, Ltd. | | 20 | 5 | 4 | 2 | 3 |
| | Alky polyglycoside | Alky polyglucoside | (Decyl glucoside) Mydol 10 | Kao Corp. | | 20 | 1 | 2 | 1 | 5 |
| | Polyoxyalkylene aryl ether | Polyoxyethylene styryl phenyl ether | Newcol 2604 | Nippon Nyukazai Co., Ltd. | 9.0 | 20 | 1 | 1 | 2 | 3 |
| | | | Newcol 2607 | Nippon Nyukazai Co., Ltd. | 11.2 | 20 | 5 | 4 | 3 | 5 |
| | | | Newcol 2609 | Nippon Nyukazai Co., Ltd. | 12.6 | 20 | 4 | 5 | 1 | 5 |
| | | | Newcol 2614 | Nippon Nyukazai Co., Ltd. | 14.7 | 20 | 5 | 3 | 3 | 3 |
| | | Polyoxyethylene alkyl phenol | (Nonyl phenol) Newcol 560 | Nippon Nyukazai Co., Ltd. | 10.9 | 20 | 1 | 1 | 1 | 5 |
| | | Polyoxyalkylene styryl phenyl ether | Newcol 2608 F | Nippon Nyukazai Co., Ltd. | 12.5 | 20 | 5 | 2 | 1 | 4 |
| | Glycerin fatty acid ester | Fatty acid mono- or diglyceride | (Glycerin monopalmitate) Poem PV-100 | Riken Vitamin Co., Ltd. | 4.3 | 20 | nt | 5 | 4 | 1 |
| | | | (Glycerin monostearate) Rikemal S-100 | Riken Vitamin Co., Ltd. | 5.3 | 20 | nt | 5 | 5 | 1 |
| | | | (Glycerin monobehenate) Rikemal B-100 | Riken Vitamin Co., Ltd. | 4.2 | 20 | 1 | 3 | 3 | 5 |
| | | | (Glycerin mono-12-hydroxystearate) Rikemal HG-100 | Riken Vitamin Co., Ltd. | 3.4 | 20 | 4 | 5 | 3 | 5 |
| | | | (Glycerol monooleate) Rikemal XO-100 | Riken Vitamin Co., Ltd. | 4.3 | 20 | nt | 1 | 1 | 1 |
| | | | (Glycerin monocaprylate) Poem M 100 | Riken Vitamin Co., Ltd. | 7.0 | 20 | 5 | 5 | 1 | 1 |
| | | | (Glycerin monocaprate) Poem M-200 | Riken Vitamin Co., Ltd. | 6.8 | 20 | 1 | 5 | 1 | 5 |
| | | | (Glycerin monolaurate) Poem M-300 | Riken Vitamin Co., Ltd. | 5.4 | 20 | 5 | 5 | 2 | 1 |
| | | | (Glycerin mono/distearate) Rikemal S-200 | Riken Vitamin Co., Ltd. | 3.2 | 20 | nt | 5 | 5 | 1 |
| | | | (Glycerin mono/dipalmitate) Poem P-200 | Riken Vitamin Co., Ltd. | 3.2 | 20 | 1 | 2 | 4 | 4 |
| | | | (Glycerin mono/dibehenate) Poem B-200 | Riken Vitamin Co., Ltd. | 2.8 | 20 | 1 | 1 | 4 | 3 |
| | | | (Glycerin mono/dioleate) Poem OL-200 | Riken Vitamin Co., Ltd. | 3.1 | 20 | 1 | 1 | 1 | 2 |
| | | | (Glycerin diacetomonolaurate) Poem G-002 | Riken Vitamin Co., Ltd. | | 20 | 1 | 1 | 4 | 1 |
| | | | (Glycerin diacetomonooleate) Poem G-038 | Riken Vitamin Co., Ltd. | | 20 | 1 | 1 | 1 | 1 |

TABLE 5-continued

Test Example 5: Nonionic Surfactants

| Broad Classification | Intermediate Classification | Narrow Classification | Product Name | Supplier | HLB | Assistant Content (parts) | Evaluation Score ||||
|---|---|---|---|---|---|---|---|---|---|---|
| | | | | | | | CDM | VDM | CPM | WR |
| | | Glycerin organic acid fatty acid ester | (Acetic acid monoglyceride) | Poem G-508 | Riken Vitamin Co., Ltd. | 0.8 | 20 | 5 | 5 | 5 | 1 |
| | | | (Citric acid fatty acid monoglycerice) | Poem K-90 | Riken Vitamin Co., Ltd. | | 20 | nt | 1 | 1 | 1 |
| | | | (Citric acid fatty acid monoglycerice) | Poem K-37V | Riken Vitamin Co., Ltd. | | 20 | 5 | 5 | 2 | 1 |
| | | | (Succinic acid organic acid monoglyceride) | Poem B-10 | Riken Vitamin Co., Ltd. | | 20 | nt | 3 | 4 | 1 |
| | | | (Diacetyl tartrate organic acid monoglyceride) | Poem W-60 | Riken Vitamin Co., Ltd. | | 20 | nt | 5 | 4 | 1 |
| | | Medium-chain fatty acid triglyceride | | Actor M-1 | Riken Vitamin Co., Ltd. | | 20 | 5 | 3 | 5 | 4 |
| | | | | Actor M-2 | Riken Vitamin Co., Ltd. | | 20 | 5 | 1 | 4 | 4 |
| | | | | Actor M-3 | Riken Vitamin Co., Ltd. | | 20 | 5 | 1 | 4 | 3 |
| | | | | Actor M-4 | Riken Vitamin Co., Ltd. | | 20 | 5 | 1 | 4 | 3 |
| Polyglycerin fatty acid ester | Polyglycerin fatty acid ester | (Digylcerin monostearate) | Rikemal S-71-D | Riken Vitamin Co., Ltd. | 5.7 | 20 | 2 | 1 | 3 | 1 |
| | | (Digylcerin monolaurate) | Poem DL 100 | Riken Vitamin Co., Ltd. | 9.4 | 20 | 2 | 2 | 4 | 5 |
| | | (Digylcerin monomyristate) | Poem DM-100 | Riken Vitamin Co., Ltd. | 8.7 | 20 | 5 | 3 | 4 | 5 |
| | | (Digylcerin monostearate) | Poem DS-100A | Riken Vitamin Co., Ltd. | 7.7 | 20 | 5 | 5 | 4 | 2 |
| | | (Digylcerin monooleate) | Poem DO 100V | Riken Vitamin Co., Ltd. | 7.3 | 20 | 2 | 3 | 4 | 5 |
| | | (Tetraglycerin stearate) | Poem J-4081V | Riken Vitamin Co., Ltd. | 5.6 | 20 | 3 | 1 | 1 | 1 |
| | | (Decaglycerin laurate) | Poem J-0021 | Riken Vitamin Co., Ltd. | 15.5 | 20 | 5 | 5 | 2 | 4 |
| | | (Tetraglycerin stearate) | Poem J-0081HV | Riken Vitamin Co., Ltd. | 12 | 20 | 5 | 3 | 1 | 2 |
| | | (Polyglycerin polyricinoleate) | Poem PR-100 | Riken Vitamin Co., Ltd. | 0.5 | 20 | 5 | 5 | 2 | 1 |
| Propylene glycol fatty acid ester | Propylene glycol fatty acid aster | (PG monolaurate) | Rikemal PL 100 | Riken Vitamin Co., Ltd. | 4.2 | 20 | 5 | 5 | 1 | 5 |
| | | (PG monopalmitate) | Rikemal PP-100 | Riken Vitamin Co., Ltd. | 3.8 | 20 | nt | 4 | 4 | 1 |
| | | (PG monostearate) | Rikemal PS-100 | Riken Vitamin Co., Ltd. | 3.7 | 20 | nt | 1 | 5 | 1 |
| | | (PG monooleate) | Rikemal PO-100V | Riken Vitamin Co., Ltd. | 3.6 | 20 | nt | 1 | 1 | 2 |
| Sorbitan fatty acid ester | Sorbitan fatty acid ester | (Sorbitan monolaurate) | Newcol 20 | Nippon Nyukazai Co., Ltd. | 8.1 | 20 | 2 | 5 | 1 | 5 |
| | | (Sorbitan monolaurate) | Rikemal L-250A | Riken Vitamin Co., Ltd. | 7.4 | 20 | 1 | 5 | 1 | 5 |
| | | (Sorbitan monopalmitate) | Rikemal P-300 | Riken Vitamin Co., Ltd. | 5.6 | 20 | nt | 3 | 1 | 1 |
| | | (Sorbitan monostearate) | Rikemal S 300(W) | Riken Vitamin Co., Ltd. | 5.0 | 20 | nt | 5 | 4 | 1 |
| | | (Sorbitan tristearate) | Poem S-65V | Riken Vitamin Co., Ltd. | 3.0 | 20 | nt | 4 | 4 | 1 |
| | | (Sorbitan monooleate) | Poem O-80V | Riken Vitamin Co., Ltd. | 4.9 | 20 | 5 | 5 | 2 | 2 |
| Polyoxyethylene sorbitan fatty acid ester | Polyoxyethylene sorbitan fatty acid ester | (POE 20 sorbitan monolaurate) | | Wako Pure Chemica Industries, Ltd. | | 20 | 5 | 4 | 2 | 1 |
| | | (POE 20 sorbitan monostearate) | | Wako Pure Chemica Industries, Ltd. | | 20 | 2 | 3 | 1 | 1 |
| | | (POE 20 sorbitan tristearate) | | Wako Pure Chemica Industries, Ltd. | | 20 | 1 | 3 | 4 | 1 |

TABLE 5-continued

Test Example 5: Nonionic Surfactants

| Broad Classification | Intermediate Classification | Narrow Classification | Product Name | Supplier | HLB | Assistant Content (parts) | Evaluation Score CDM | VDM | CPM | WR |
|---|---|---|---|---|---|---|---|---|---|---|
| | | (POE 20 sortidan oleate) | Newcol 85 | Nippon Nyukazai Co., Ltd. | 15.1 | 20 | 3 | 5 | 3 | 1 |
| | | (POE 20 sorbitan oleate) | Newcol 82 | Nippon Nyukazai Co., Ltd. | 12.0 | 20 | 2 | 1 | 1 | 1 |
| | | (POE 20 sorbitan monooleate) | | Wako Pure Chemica Industries, Ltd. | | 20 | 5 | 3 | 1 | 1 |
| | Fatty acid dietnanolamine | Fatty acid dietnanolamide | Aminon PK-025 | Kao Corp. | | 20 | 1 | 5 | 4 | 5 |
| | Alky imidazoline | Alky imidazoline | Homogenol L-95 | Kao Corp. | | 20 | 1 | 5 | 1 | 5 |
| | Fluorine-based surfactant | Fluorine-based surfactant | (Perfluoroalkyl carboxylic acid) | Surflor S-241 | AGC Selmi Chemical Co., Ltd. | | 20 | 1 | 1 | 1 | 1 |
| | Silicone based surfactant | Silicone based surfactant | (Silicone modified oil) | ANTIFOAM 95 | Dow Corning Toray Co., Ltd. | | 20 | 1 | 1 | 1 | 1 |
| | Acetylene glycol-based | Acetylene glycol-based surfactant | | Surfynol 104S | Nissin Chemical Co., Ltd. | | 20 | 1 | 1 | 1 | 1 |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

[Test Example 6] Evaluation of Compositions Containing Anionic, Cationic or Amphoteric Surfactant (Water-Soluble Powders)

The effects of the D-tagatose water-soluble powders containing anionic surfactant, cationic surfactant or amphoteric surfactant prepared in Example 6 against cucumber downy mildew, grape vine downy mildew, cucumber powdery mildew and wheat rust were evaluated using the same test method and evaluation method as Test Example 1. The improvement in efficacy with respect to cucumber downy mildew was evaluated based on the control effect of a 200-fold dilution (treatment concentrations: D-tagatose 0.4%+assistant 0.1%), while the improvement in efficacy with respect to other diseases was evaluated based on the control effect of a 100-fold dilution (treatment concentrations: D-tagatose 0.8%+assistant: 0.2%). Those results are shown in Table 6.

Remarkable improvements in control effects against cucumber downy mildew, grave vine downy mildew, cucumber powdery mildew and wheat rust were observed with formulas containing as assistants anionic surfactants selected from aryl sulfonates, formalin condensates of aryl sulfonates, α-olefin sulfonates, alkyl sulfates, sulfosuccinates, polyoxyalkylene aryl ether sulfates, polyoxyalkylene alkyl ether sulfates, polyoxyalkylene alkyl ether acetates, polyoxyalkylene aryl ether phosphates, polyoxyalkylene alkyl ether phosphates, methyl taurate and polycarboxylates, cationic surfactants selected from alkyl amine salts and quaternary ammonium salts, and amphoteric surfactants selected from alkyl betaines, amine oxides and lecithins with respect to a formula containing only D-tagatose as monosaccharide. On the other hand, remarkable improvements in control effects were not observed with formulas containing lignin sulfonate-based surfactants.

TABLE 6

Test Example 6: Anionic, Cationic and Amphoteric Surfactants

| Broad Classification | Intermediate Classification | Narrow Classification | Product Name | Supplier | Assistant Content (parts) | Evaluation Score CDM | VDM | CPM | WR |
|---|---|---|---|---|---|---|---|---|---|
| Anionic surfactant | Aryl sulfonate | Alkyl benzene sulfonate (Sodium dodecyl benzene sulfonate) | Neoflex No. 6F | Kao Corp. | 20 | 5 | 5 | 5 | 5 |
| | | Alkyl naphthalene sulfonate (Sodium diallyl naphthalene sulfonate) | New Kalgen BX-C | Takemoto Oil & Fat Co., Ltd. | 20 | 1 | 4 | 3 | 4 |
| | Formalin condensate of aryl sulfonate | Naphthalene sulfonate formalin condensate (Sodium alkyl naphthalene sulfonate) | New Kalgen WG-1 | Takemoto Oil & Fat Co., Ltd. | 20 | 1 | 3 | 3 | 5 |
| | | Naphthalene sulfonate formalin condensate (Sodium β-naphthalene sulfonate formalin condensate) | Demol RN | Kao Corp. | 20 | 5 | 5 | 4 | 1 |
| | | Alkyl naphthalene sulfonate formalin condensate (Sodium alkyl naphthalene sulfonate formalin condensate) | Raberin FAN | Daiichi Kogyo Seiyaku Co., Ltd. | 20 | 5 | 5 | 4 | 1 |
| | | Alkyl naphthalene sulfonate formalin condensate | Morwet D425 | Lion Akzo Co., Ltd. | 20 | 5 | 5 | 4 | 1 |
| | | Phenol sulfonate (Sodium phenol sulfonate formalin condensate) | Tamol DN | BASF Corp. | 20 | 5 | 5 | 3 | 1 |
| | α-Olefin sulfonate | Sodium α-olefin sulfonate | M-3801G | Daiichi Kogyo Seiyaku Co., Ltd. | 20 | 5 | 5 | 4 | 4 |
| | Alkyl sulfate | (Sodium lauryl sulfate) | Emal 10PT | Kao Corp. | 20 | 5 | 5 | 5 | 5 |
| | Sulfosuccinate | Dialkyl sulfosuccinate | Gelopon SDS | Rhodia Nicca Ltd. | 20 | 5 | 4 | 5 | 5 |
| | Polyoxyalkylene aryl ether sulfate | Polyoxyethylene alkyl aryl ether sulfate (N.P.NH$_4$ salt) | Newcol 291PGPM | Nippon Nyukazai Co., Ltd. | 20 | 5 | 5 | 4 | 5 |
| | | Polyoxyethylene styryl phenyl ether sulfate (Tristearyl NH$_4$ salt) | Newcol 560SFC | Nippon Nyukazai Co., Ltd. | 20 | 4 | 1 | 3 | 5 |
| | | Polyoxyalkylene styryl phenyl ether sulfate (POA allyl phenyl NH$_4$ salt) | Solpol T-15SPG | Toho Chemical Industry Co., Ltd. | 20 | 3 | 1 | 1 | 3 |
| | | Polyoxyalkylene styryl phenyl ether sulfate (POA allyl phenyl NH$_4$ salt) | New Kalgen FS-700PG | Takemoto Oil & Fat Co., Ltd. | 20 | 2 | 1 | 1 | 1 |
| | Polyoxyethylene alkyl ether sulfate | Polyoxyethylene alkyl ether sulfate (Sodium polyoxyethylene lauryl ether sulfate) | New Kalgen FS-7PG | Takemoto Oil & Fat Co., Ltd. | 20 | 5 | 1 | 1 | 1 |
| | | (Sodium polyoxyethylene lauryl ether sulfate) | Emal E-27C | Kao Corp. | 20 | 4 | 1 | 4 | 4 |
| | Polyoxyethylene alkyl ether acetate | Polyoxyethylene alkyl ether acetate | Kao Akypo RLM-100NV | Kao Corp. | 20 | 1 | 1 | 1 | 4 |
| | Polyoxyalkylene aryl ether phosphate | Polyoxyethylene styrenated phenyl ether phosphate (Tristearyl) | New Kalgen FS-3PG | Takemoto Oil & Fat Co., Ltd. | 20 | 4 | 3 | 2 | 4 |
| | | Polyoxyethylene styrenated phenyl ether phosphate ester (Monoethanolamine salt) | Prisurf AL | Daiichi Kogyo Seiyaku Co., Ltd. | 20 | 5 | 4 | 1 | 5 |
| | Polyoxyethylene alkyl ether phosphate | Polyoxyethylene lauryl ether phosphate | Prisurf DB-01 | Daiichi Kogyo Seiyaku Co., Ltd. | 20 | 2 | 3 | 5 | 4 |
| | | Poyoxyethylene alkyl ether phosphate | GERONOL CF/AR | Rhodia Nicca Ltd. | 20 | 1 | 1 | 4 | 1 |
| | | Polyoxyethylene lauryl ether phosphate ester | Prisurf A208B | Daiichi Kogyo Seiyaku Co., Ltd. | 20 | 1 | 5 | 4 | 5 |
| | | Polyoxyalkylene alkyl ether phosphate ester | Antox EHD-PNA | Nippon Nyukazai Co., Ltd. | 20 | 3 | 4 | 5 | 5 |
| | Methyl taurate | Sodium oleyl methyl taurate | Hostapon TPHC | Clariant Japan K.K. | 20 | 1 | 3 | 4 | 3 |
| | Polycarboxylate | Sodium alkylene maleic acid copolymer | Demol EP Powder | Kao Corp. | 20 | 2 | 1 | 1 | 1 |
| | | (Maleic acid-isobutylene copolymer) | New Kalgen WG-5 | Takemoto Oil & Fat Co., Ltd. | 20 | 5 | 5 | 3 | 1 |
| | | Sodium acrylate-maleic acid copolymer | Sokalan CP5 | BASF Corp. | 20 | 1 | 1 | 3 | 1 |
| | | Sodium polycarboxylate + distyryl phenyl ether sulfate NH$_4$ salt | Gelopon SC/213 | Rhodia Nicca Ltd. | 20 | 1 | 1 | 1 | 1 |

TABLE 6-continued

Test Example 6: Anionic, Cationic and Amphoteric Surfactants

| Broad Classification | Intermediate Classification | Narrow Classification | Product Name | Supplier | Assistant Content (parts) | Evaluation Score CDM | VDM | CPM | WR |
|---|---|---|---|---|---|---|---|---|---|
| | Lignin sulfonate | Calcium lignin sulfonate | San Extract P201 | Nippon Paper Industries Co., Ltd. | 20 | 1 | 0 | 1 | 0 |
| | | High-purity, high molecular weight calcium lignin sulfonate | Pearl Ex CP | Nippon Paper Industries Co., Ltd. | 20 | 1 | 1 | 1 | 0 |
| | | Sodium lignin sulfonate | San Extract P252 | Nippon Paper Industries Co., Ltd. | 20 | 0 | 0 | 1 | 0 |
| | | High-purity, high molecular weight sodium lignin sulfonate | Pearl Ex NP | Nippon Paper Industries Co., Ltd. | 20 | 0 | 0 | 0 | 0 |
| | | High-purity, partially desulfonated sodium lignin sulfonate | Vanilex N | Nippon Paper Industries Co., Ltd. | 20 | 0 | 0 | 0 | 0 |
| | | Lignin sulfonate | REAX 88A | Westvaco Corp. | 20 | 0 | 0 | 0 | 0 |
| Cationic surfactant | Alkyl amine salt | Coconut amine acetate | Acetamin 24 | Kao Corp. | 20 | 5 | 5 | 1 | 5 |
| | | Stearyl amine acetate | Acetamin 86 | Kao Corp. | 20 | 2 | 5 | 5 | 1 |
| | Quaternary ammonium salt | Didecyl dimethyl ammonium chloride | Alucard 210-80E | Lion Akzo Co., Ltd. | 20 | 5 | 5 | 5 | 5 |
| | | Oleylbis(2-hydroxyethyl)methyl ammonium chloride | Ethoquad O/12 | Lion Akzo Co., Ltd. | 20 | 5 | 5 | 4 | 5 |
| Amphoteric surfactant | Alkyl betaine | Lauryl betaine | Amphitol 24B | Kao Corp. | 20 | 4 | 4 | 1 | 5 |
| | Amino oxide | Lauryl dimethyl amino oxide | Amphitol 20N | Kao Corp. | 20 | 5 | 4 | 5 | 5 |
| | Lecithin | Lecithins (glycerophospholipid) (Soybean lecithin) | | Wako Pure Chemical Industries, Ltd. | 20 | 5 | 3 | 1 | 1 |
| | | (Egg yolk lecithin) | | Wako Pure Chemical Industries, Ltd. | 20 | 5 | 5 | 2 | 1 |

5: Improvement in preventive value of 40 or more
4: Improvement in preventive value of 30 to less than 40
3: Improvement in preventive value of 20 to less than 30
2: Improvement in preventive value of 10 to less than 20
1: Improvemen in preventive value of 1 to less than 10
0: Equal or decrease in preventive value
nt: Not tested

[Test Example 7] Evaluation of Compositions Containing Water-Soluble Polymer (Water-Soluble Powders)

The effects of the D-tagatose water-soluble powders containing water-soluble polymers prepared in Example 7 against cucumber downy mildew, grape vine downy mildew, cucumber powdery mildew and wheat rust were evaluated using the same test method and evaluation method as Test Example 1. The improvement in efficacy with respect to cucumber downy mildew was evaluated based on the control effect of a 200-fold dilution (treatment concentrations: D-tagatose 0.4%+assistant 0.1%), while the improvement in efficacy with respect to grape vine downy mildew, cucumber powdery mildew and wheat rust was evaluated based on the control effect of a 100-fold dilution (treatment concentrations: D-tagatose 0.8%+assistant: 0.2%). Those results are shown in Table 7.

Remarkable improvements in control effects against cucumber downy mildew, grave vine downy mildew, and cucumber powdery mildew were observed with formulas containing as assistants water-soluble polymers selected from polyoxyalkylene, dextrin, alpha starch, etherified starch, xanthan gum, guar gum and polyvinylpyrrolidone with respect to a formula containing only D-tagatose as monosaccharide.

[Test Example 8] Evaluation of Compositions Containing Sugars or Amino Acids (Liquid Preparations)

Enhancement of the efficacy of the D-tagatose liquid preparations containing amino acids, amino sugars or disaccharide alcohols prepared in Example 8 against cucumber downy mildew were evaluated using the same test method and evaluation method as Test Example 1 based on the control effect of a 10-fold dilution (treatment concentrations: D-tagatose 0.5%+assistant 0.5%). Those results are shown in Table 8.

Improvements in control effects against cucumber downy mildew were observed with formulas containing as assistants amino acids or sugars with respect to a formula containing only D-tagatose as monosaccharide. In the case of amino acids, improvement of control effects were particularly remarkable with formulas containing amino acids selected from L-aspartic acid, L-glutamic acid, glycine, β-alanine and L-pyroglutamic acid. In addition, in the case of sugars, remarkable improvement of control effects were observed with formulas containing amino sugars selected from D-glucosamine hydrochloride and D-galactosamine hydrochloride or containing disaccharide alcohols selected from isomalt, maltitol and lactitol in comparison with formulas containing other sugars. On the other hand, remarkable improvement of control effects was not observed with formulas containing nucleic acid bases, nucleotides or organic acids.

TABLE 7

Test Example 7: Water-Soluble Polymers

| Broad Classification | Intermediate Classification | Narrow Classification | Product Name | Supplier | Assistant Content (parts) | Evaluation Score | | | |
|---|---|---|---|---|---|---|---|---|---|
| | | | | | | CDM | VDM | CPM | WR |
| Water-soluble polymer | Acrylic polymer | Sodium polyacrylate | Sokalan PA-40 | BASF | 20 | 3 | nt | 3 | nt |
| | | Sodium polymethacrylate ((Meth)acrylate copolymer) | Disrol AQ-3 | Nippon Nyukazai Co., Ltd. | 20 | 2 | nt | 3 | nt |
| | Polyoxy-alkylene | Polyoxyethylene (Polyethylene glycol) | PEG200 | Daiichi Kogyo Seiyaku Co., Ltd. | 20 | 5 | nt | 1 | nt |
| | Cellulose derivative | Methyl cellulose | Metolose SM-25 | Shin-Etsu Chemical Co., Ltd. | 20 | 1 | nt | 3 | nt |
| | Modified starch | Dextrin | Amycol No. 1 | Nippon Starch Chemical Co., Ltd. | 20 | 5 | nt | 1 | nt |
| | | Dextrin | Oil Q No. 50 | Nippon Starch Chemical Co., Ltd. | 20 | 2 | 5 | 1 | 3 |
| | | Alpha starch (Non-modified alpha starch) | Amycol HF | Nippon Starch Chemical Co., Ltd. | 20 | 5 | nt | 1 | nt |
| | | Soluble starch | Lustergen FO | Nippon Starch Chemical Co., Ltd. | 20 | 1 | nt | 2 | nt |
| | | Etherified starch (Carboxy-methylated starch) | Kiprogum M-800A | Nippon Starch Chemical Co., Ltd. | 20 | 5 | nt | 4 | nt |
| | | Esterified starch (Phosphate-esterified starch) | Bribine | Nippon Starch Chemical Co., Ltd. | 20 | 4 | nt | 3 | nt |
| | Natural polymer | Xanthan gum | Rhodopol 23 | Rhodia Nikka Ltd. | 20 | 5 | nt | 3 | nt |
| | | Gua gum | Gua Gum | Reagent | 20 | 1 | 5 | 1 | 1 |
| | | Sodium alginate | Na Alginate | Reagent | 20 | 2 | nt | 1 | nt |
| | Synthetic polymer | Polyvinyl alcohol | Gohsenol GL-05S | Nippon Synthetic Chemical Industry Co., Ltd. | 20 | 1 | 1 | 1 | 1 |
| | | Polyvinyl-pyrrolidone | Sokalan HP50 | BASF Corp. | 20 | 1 | 4 | 1 | 1 |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

TABLE 8

Test Example 8: Sugars and Amino Acids

| Broad Classification | Intermediate Classification | Compound Name (Assistant) | Assistant Content (parts) | Evaluation Score CDM |
|---|---|---|---|---|
| Sugar | Monosaccharide | D-glyceraldehyde | 5 | 4 |
| | | D-xylulose | 5 | 1 |
| | | D-ribose | 5 | 2 |
| | | D-arabinose | 5 | 1 |
| | | D-xylose | 5 | 1 |
| | | 2-deoxy-D-ribose | 5 | 4 |
| | | D-psicose | 5 | 3 |
| | | D-sorbose | 5 | 2 |
| | | D-fructose | 5 | 2 |
| | | D-talose | 5 | 2 |
| | | D-altrose | 5 | 4 |
| | | D-glucose | 5 | 1 |
| | | D-galactose | 5 | 1 |
| | | D-mannose | 5 | 2 |
| | | D-fucose | 5 | 2 |
| | | L-fucose | 5 | 2 |
| | | L-rhamnose | 5 | 2 |
| | Disaccharide | Sucrose | 5 | 1 |
| | | Lactose | 5 | 1 |
| | | Maltose | 5 | 1 |
| | | Cellobiose | 5 | 1 |
| | | Trehalose | 5 | 3 |
| | | Maltulose | 5 | 1 |
| | Trisaccharide | Raffinose | 5 | 4 |
| | Tetrasaccharide | Stachyose | 5 | 1 |
| | Monosaccharide alcohol | D-altritol (D-talitol) | 5 | 3 |
| | | Allitol | 5 | 2 |
| | | D-sorbitol | 5 | 1 |
| | | D-mannitol | 5 | 1 |
| | | Xylitol | 5 | 2 |
| | | Meso-erythritol | 5 | 3 |
| | Disaccharide alcohol | Isomalt (palatinit) | 5 | 5 |
| | | Maltitol | 5 | 5 |
| | | Lactitol | 5 | 5 |
| | Amino sugar | D-glucosamine hydrochloride | 5 | 5 |
| | | D-galactosamine hydrochloride | 5 | 5 |
| | Sugar Analogue | Sodium D-glucuronate | 5 | 1 |
| | | D-galacturonic acid | 5 | 3 |
| | | D-gluconolactone | 5 | 2 |
| | | D-gluconic acid | 5 | 2 |
| Amino Acid | Amino acid | L-alanine | 5 | 2 |
| | | L-arginine | 5 | 1 |
| | | L-asparagine | 5 | 1 |
| | | L-aspartic acid | 5 | 5 |
| | | L-cysteine | 5 | 3 |
| | | L-serine | 5 | 1 |
| | | L-glutamic acid | 5 | 5 |
| | | L-glutamine | 5 | 1 |
| | | Glycine | 5 | 5 |
| | | L-histidine | 5 | 3 |
| | | L-isoleucine | 5 | 1 |
| | | L-leucine | 5 | 3 |
| | | L-lysine | 5 | 1 |
| | | L-threonine | 5 | 1 |
| | | L-methionine | 5 | 2 |
| | | L-phenylalanine | 5 | 3 |
| | | L-proline | 5 | 1 |
| | | L-valine | 5 | 3 |
| | | β-alanine | 5 | 5 |
| | | L-pyroglutamic acid | 5 | 4 |
| | | L-ornithine | 5 | 3 |
| | | DL-carnitine | 5 | 2 |
| Other | Nucleic acid base | Adenine | 5 | 0 |
| | | Cytosine | 5 | 0 |
| | | Guanine | 5 | 0 |
| | | Uracil | 5 | 1 |
| | Nucleoside | Uridine | 5 | 0 |
| | | Guanosine | 5 | 0 |
| | | Adenosine | 5 | 0 |
| | | Cytidine | 5 | 1 |

TABLE 8-continued

Test Example 8: Sugars and Amino Acids

| Broad Classification | Intermediate Classification | Compound Name (Assistant) | Assistant Content (parts) | Evaluation Score CDM |
|---|---|---|---|---|
| | Organic acid | Benzoic acid | 5 | 0 |
| | | Glutaric acid | 5 | 0 |
| | | Malonic acid | 5 | 0 |
| | | Acetic acid | 5 | 1 |
| | | Lactic acid | 5 | 0 |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

[Test Example 9] Evaluation of Compositions Containing Various Monosaccharides Other than D-Tagatose and Various Anionic Surfactants (Liquid Preparations)

Enhancement of the efficacy of the D-psicose, D-sorbose, D-allose, D-talose, D-galactose, D-mannose or L-fructose liquid preparations containing anionic surfactants prepared in Example 9 against grape vine downy mildew, tomato late blight, apple scab, rice blast, rice sheath blight, tomato gray mold, cucumber powdery mildew and tomato bacterial wilt were evaluated using the same test method and evaluation method as Test Example 1 based on the control effect of a 10-fold dilution (treatment concentrations: monosaccharide 1%+assistant 0.025% to 0.05%). Those results are shown in Table 9.

Remarkable improvement in control effects against grape vine downy mildew, tomato late blight, apple scab, rice plant, rice sheath blight, tomato gray mold, cucumber powdery mildew and tomato bacterial wilt were observed with formulas containing as assistants anionic surfactants selected from aryl sulfonates, formalin condensates of aryl sulfonates, alkyl sulfates, polycarboxylates and sulfosuccinates with respect to formulas containing only D-psicose, D-sorbose, D-allose, D-talose, D-galactose, D-mannose or L-fructose as monosaccharide.

TABLE 9

Test Example 5: Other Monosaccharides

| Compound (Monosaccharide) Content (%) | Anionic Surfactant | | | | Assistant Content (parts) | Water Content (parts) | Evaluation Score | | | | | | | | |
|---|---|---|---|---|---|---|---|---|---|---|---|---|---|---|---|
| | Intermediate Classification | Narrow Classification | Product Name | Supplier | | | VDM | LB | AS | B | SB | GM | CPM | TBW |
| D-psicose 10% | Aryl sulfonate | Alkyl benzene sulfonate (Sodium dodecyl benzene sulfonate) | Neopelex No. 6F | Kao Corp. | 0.25 | 89.75 | 5 | 2 | 5 | 4 | 1 | 3 | 1 | nt |
| | Aryl sulfonate formalin condensate | Alkyl naphthalene sulfonate (Sodium alkyl naphthalene sulfonate formalin condensate) | Morwet D425 | Lion Akzo Co., Ltd. | 0.5 | 89.5 | 1 | 3 | 5 | 3 | 1 | 1 | 1 | nt |
| | Alkyl sulfate | (Sodium lauryl sulfate) | Emal 10PT | Kao Corp. | 0.25 | 89.75 | 5 | 4 | 4 | 3 | 1 | 3 | 1 | nt |
| | Polycarboxylate | (Sodium acrylate/maleate copolymer) | Sokalan CP5 | BASF Corp. | 0.5 | 89.5 | 1 | nt | nt | nt | nt | nt | 2 | nt |
| | Sulfosuccinate | Dialkyl sulfosuccinate | Gelopon SDS | Rhodia Nicca Ltd. | 0.5 | 89.5 | 1 | nt | nt | nt | nt | nt | 5 | nt |
| | | | Newcol 292PGPM | Nippon Nyukazai Co., Ltd. | 0.5 | 89.5 | 1 | nt | nt | nt | nt | nt | 1 | nt |
| | No assistant, ( ) indicate preventive values | | | | 0 | 90 | (0) | (47) | (50) | (50) | (40) | (50) | (17) | |
| D-sorbose 10% | Aryl sulfonate | Alkyl benzene sulfonate (Sodium dodecyl benzene sulfonate) | Neopelex No. 6F | Kao Corp. | 0.25 | 89.75 | 4 | 1 | 5 | 5 | 1 | 4 | 3 | nt |
| | Aryl sulfonate formalin condensate | Alkyl naphthalene sulfonate (Sodium alkyl naphthalene sulfonate formalin condensate) | Morwet D425 | Lion Akzo Co., Ltd. | 0.5 | 89.5 | 4 | 5 | 5 | 5 | 1 | 3 | 1 | nt |
| | Alkyl sulfate | (Sodium lauryl sulfate) | Emal 10PT | Kao Corp. | 0.25 | 89.75 | 5 | 3 | 4 | 5 | 1 | 1 | 3 | nt |
| | Polycarboxylate | (Sodium acrylate/maleate copolymer) | Sokalan CP5 | BASF Corp. | 0.5 | 89.5 | 1 | nt | nt | nt | nt | nt | 1 | nt |
| | Sulfosuccinate | Dialkyl sulfosuccinate | Gelopon SDS | Rhodia Nicca Ltd. | 0.5 | 89.5 | 1 | nt | nt | nt | nt | nt | 2 | nt |
| | | | Newcol 292PGPM | Nippon Nyukazai Co., Ltd. | 0.5 | 89.5 | 1 | nt | nt | nt | nt | nt | 1 | nt |
| | No assistant, ( ) indicate preventive values | | | | 0 | 90 | (0) | (33) | (33) | (17) | (40) | (33) | (17) | |
| D-allose 10% | Aryl sulfonate | Alkyl benzene sulfonate (Sodium dodecyl benzene sulfonate) | Neopelex No. 6F | Kao Corp. | 0.25 | 89.75 | 1 | 1 | 5 | 4 | 2 | 1 | 1 | nt |
| | Aryl sulfonate formalin condensate | Alkyl naphthalene sulfonate (Sodium alkyl naphthalene sulfonate formalin condensate) | Morwet D425 | Lion Akzo Co., Ltd. | 0.5 | 89.5 | 5 | 2 | 5 | 3 | 3 | 1 | 3 | nt |
| | Alkyl sulfate | (Sodium lauryl sulfate) | Emal 10PT | Kao Corp. | 0.25 | 89.75 | 5 | 2 | 5 | 3 | 2 | 1 | 2 | nt |
| | Polycarboxylate | (Sodium acrylate/maleate copolymer) | Sokalan CP5 | BASF Corp. | 0.5 | 89.5 | 1 | nt | nt | nt | nt | nt | 2 | nt |
| | Sulfosuccinate | Dialkyl sulfosuccinate | Gelopon SDS | Rhodia Nicca Ltd. | 0.5 | 89.5 | 1 | nt | nt | nt | nt | nt | 3 | nt |
| | | | Newcol 292PGPM | Nippon Nyukazai Co., Ltd. | 0.5 | 89.5 | 1 | nt | nt | nt | nt | nt | 1 | nt |
| | No assistant, ( ) indicate preventive values | | | | 0 | 90 | (40) | (60) | (66) | (40) | (60) | (33) | (17) | |
| D-talose 10% | Aryl sulfonate | Alkyl benzene sulfonate (Sodium dodecyl benzene sulfonate) | Neopelex No. 6F | Kao Corp. | 0.25 | 89.75 | 4 | nt | nt | 4 | 3 | nt | 3 | nt |
| | Aryl sulfonate formalin condensate | Alkyl naphthalene sulfonate (Sodium alkyl naphthalene sulfonate formalin condensate) | Morwet D425 | Lion Akzo Co., Ltd. | 0.5 | 89.5 | 4 | nt | nt | 3 | 3 | nt | 4 | nt |
| | Alkyl sulfate | (Sodium lauryl sulfate) | Emal 10PT | Kao Corp. | 0.25 | 89.75 | 5 | nt | nt | 3 | 3 | nt | 4 | nt |
| | Polycarboxylate | (Sodium acrylate/maleate copolymer) | Sokalan CP5 | BASF Corp. | 0.5 | 89.5 | 1 | nt | nt | nt | nt | nt | 1 | nt |
| | Sulfosuccinate | Dialkyl sulfosuccinate | Gelopon SDS | Rhodia Nicca Ltd. | 0.5 | 89.5 | 1 | nt | nt | nt | nt | nt | 5 | nt |
| | | | Newcol 292PGPM | Nippon Nyukazai Co., Ltd. | 0.5 | 89.5 | 1 | nt | nt | nt | nt | nt | 1 | nt |
| | No assistant, ( ) indicate preventive values | | | | 0 | 90 | (0) | | | (50) | (30) | | (17) | |

TABLE 9-continued

Test Example 5: Other Monosaccharides

| Compound (Monosaccharide) Content (%) | Anionic Surfactant | | | | Assistant Content (parts) | Water Content (parts) | Evaluation Score | | | | | | | |
|---|---|---|---|---|---|---|---|---|---|---|---|---|---|---|
| | Intermediate Classification | Narrow Classification | Product Name | Supplier | | | VDM | LB | AS | B | SB | GM | CPM | TBW |
| D-galactose 10% | Aryl sulfonate | Alkyl benzene sulfonate (Sodium dodecyl benzene sulfonate) | Neopelex No. 6F | Kao Corp. | 0.25 | 89.75 | 5 | 5 | 5 | 5 | 2 | 4 | 1 | 2 |
| | Aryl sulfonate formalin condensate | Alkyl naphthalene sulfonate (Sodium alkyl naphthalene sulfonate formalin condensate) | Morwet D425 | Lion Akzo Co., Ltd. | 0.5 | 89.5 | 1 | 5 | 5 | 5 | 3 | 4 | 5 | nt |
| | Alkyl sulfate | (Sodium lauryl sulfate) | Emal 10PT | Kao Corp. | 0.25 | 89.75 | 5 | 5 | 5 | 5 | 2 | 1 | 5 | 5 |
| | Polycarboxylate | (Sodium acrylate/maleate copolymer) | Sokalan CP5 | BASF Corp. | 0.5 | 89.5 | 1 | nt | nt | nt | nt | nt | 5 | nt |
| | Sulfosuccinate | Dialkyl sulfosuccinate | Gelopon SDS | Rhodia Nicca Ltd. | 0.5 | 89.5 | 1 | nt | nt | nt | nt | nt | 5 | 2 |
| | | | Newcol 292PGPM | Nippon Nyukazai Co., Ltd. | 0.5 | 89.5 | 1 | nt | nt | nt | nt | nt | 1 | nt |
| | No assistant, ( ) indicate preventive values | | | | 0 | 90 | (0) | (0) | (66) | (17) | (60) | (33) | (0) | (25) |
| L-fructose 10% | Aryl sulfonate | Alkyl benzene sulfonate (Sodium dodecyl benzene sulfonate) | Neopelex No. 6F | Kao Corp. | 0.25 | 89.75 | 1 | nt | nt | 5 | 2 | 2 | 2 | nt |
| | Aryl sulfonate formalin condensate | Alkyl naphthalene sulfonate (Sodium alkyl naphthalene sulfonate formalin condensate) | Morwet D425 | Lion Akzo Co., Ltd. | 0.5 | 89.5 | 5 | nt | nt | 5 | 2 | 3 | 2 | nt |
| | Alkyl sulfate | (Sodium lauryl sulfate) | Emal 10PT | Kao Corp. | 0.25 | 89.75 | 5 | nt | nt | 5 | 2 | 1 | 2 | nt |
| | Polycarboxylate | (Sodium acrylate/maleate copolymer) | Sokalan CP5 | BASF Corp. | 0.5 | 89.5 | 5 | nt | nt | nt | nt | nt | 2 | nt |
| | Sulfosuccinate | Dialkyl sulfosuccinate | Gelopon SDS | Rhodia Nicca Ltd. | 0.5 | 89.5 | 1 | nt | nt | nt | nt | nt | 2 | nt |
| | | | Newcol 292PGPM | Nippon Nyukazai Co., Ltd. | 0.5 | 89.5 | 1 | nt | nt | nt | nt | nt | 4 | nt |
| | No assistant, ( ) indicate preventive values | | | | 0 | 90 | (0) | nt | nt | (0) | (60) | (40) | (33) | nt |
| D-mannose 10% | Aryl sulfonate | Alkyl benzene sulfonate (Sodium dodecyl benzene sulfonate) | Neopelex No. 6F | Kao Corp. | 0.25 | 89.75 | nt | nt | nt | 5 | 4 | 1 | 2 | nt |
| | Aryl sulfonate formalin condensate | Alkyl naphthalene sulfonate (Sodium alkyl naphthalene sulfonate formalin condensate) | Morwet D425 | Lion Akzo Co., Ltd. | 0.5 | 89.5 | nt | nt | nt | nt | nt | nt | 2 | nt |
| | Alkyl sulfate | (Sodium lauryl sulfate) | Emal 10PT | Kao Corp. | 0.25 | 89.75 | nt | nt | nt | nt | nt | nt | 2 | nt |
| | Polycarboxylate | (Sodium acrylate/maleate copolymer) | Sokalan CP5 | BASF Corp. | 0.5 | 89.5 | nt | nt | nt | nt | nt | nt | 2 | nt |
| | Sulfosuccinate | Dialkyl sulfosuccinate | Gelopon SDS | Rhodia Nicca Ltd. | 0.5 | 89.5 | nt | nt | nt | nt | nt | nt | 4 | nt |
| | No assistant, ( ) indicate preventive values | | | | 0 | 90 | | | | (17) | (60) | (16) | (33) | |

5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value
nt: Not tested

[Test Example 10] Evaluation of Compositions Containing D-Tagatose and Multiple Types of Surfactants (Water-Soluble Powders) (Mixed Assistants)

The effects of a formula containing D-tagatose only, formulas containing D-tagatose and multiple types of surfactants prepared in Example 10, and formulas containing only multiple types of surfactants on cucumber downy mildew, grape vine downy mildew, tomato late blight, cucumber powdery mildew, barley powdery mildew, wheat rust, grape vine rust, soybean rust, tomato gray mold, rice blast, cucumber anthracnose, apple scab, wheat speckled leaf blotch, cucumber bacterial spot and cabbage soft rot were evaluated using the same test method as Test Example 1. Those results are shown in Table 10.

Protective values calculated from disease development were represented with the following indices (preventive value indices). The formulas containing D-tagatose and assistants and formulas containing assistants only were evaluated based on the control effect of a 100-fold dilution (D-tagatose 0.8%+assistant, or assistant only), while the formula containing D-tagatose only was evaluated based on the control effect of a 125-fold dilution (D-tagatose 0.8%) and a 20-fold dilution (D-tagatose 5%).

0: Preventive value of less than 30
1: Preventive value of 30 to less than 60
2: Preventive value of 60 to less than 80
3: Preventive value of 80 to less than 90
4: Preventive value of 90 to less than 95
5: Preventive value of 95 to less than 98
6: Preventive value of 98 to less than 100
7: Preventive value of 100

Although the formula containing D-tagatose only demonstrated a high control effect against cucumber downy mildew, grape vine downy mildew, cucumber powdery mildew and barley powdery mildew at a treatment concentration of 5%, those effects were not adequate at a treatment concentration of 0.8%. In addition, although this formula also demonstrated effects against tomato late blight, wheat rust, grape vine rust, soybean rust, tomato gray mold, rice blast, cucumber anthracnose, apple scab and wheat speckled leaf blotch at a treatment concentration of 5%, those effects were not adequate.

Remarkable improvement in control effects against fungal diseases such as cucumber downy mildew, grape vine downy mildew, tomato late blight, cucumber powdery mildew, barley powdery mildew, wheat scab, grape vine rust, soybean rust, tomato gray mold, rice blast, cucumber anthracnose, apple scab or wheat speckled leaf blotch was observed with formulas containing as assistants anionic surfactants selected from aryl sulfonates, formalin condensates of aryl sulfonates and alkyl sulfates with respect to the formula containing D-tagatose only. Moreover, high control effects were also demonstrated against bacterial diseases such as cucumber bacterial wilt or cabbage soft rot, for which the formula containing D-tagatose only cannot be expected to demonstrate control effects. On the other hand, effects were not demonstrated against any of the diseases by the formulas containing assistants only.

TABLE 10

| | | Test Example 10: Mixed Assistants | | | | | | | | | | | |
|---|---|---|---|---|---|---|---|---|---|---|---|---|---|
| | D-Tagatose Content | Content in Composition (parts) | | | | | | | | D-Tagatose | | | |
| | | Assistant | Assistant | Assistant | Assistant | Assistant | Assistant | Assistant | Dilution | Treatment Concen- | Preventive Value Index | | |
| No. | (parts) | A | B | C | D | E | F | G | Factor | tration | CDM | VDM | LB |
| Formula 1 | 80 | 5 | 5 | 5 | 0 | 0 | 0 | 5 | 100 | 0.8 | 5 | 3 | 3 |
| Formula 2 | 80 | 2.5 | 5 | 5 | 0 | 0 | 0 | 7.5 | 100 | 0.8 | 6 | 6 | 4 |
| Formula 3 | 80 | 5 | 5 | 2.5 | 0 | 0 | 0 | 7.5 | 100 | 0.8 | 4 | 5 | 5 |
| Formula 4 | 80 | 2.5 | 2.5 | 2.5 | 0 | 0 | 0 | 12.5 | 100 | 0.8 | 4 | 4 | 3 |
| Formula 5 | 80 | 1 | 5 | 0 | 10 | 0 | 0 | 4 | 100 | 0.8 | 6 | 7 | 4 |
| Formula 6 | 80 | 1 | 5 | 3 | 10 | 0 | 0 | 1 | 100 | 0.8 | 6 | 7 | 4 |
| Formula 7 | 80 | 1 | 5 | 0 | 0 | 10 | 0 | 4 | 100 | 0.8 | 6 | 4 | 3 |
| Formula 8 | 80 | 1 | 5 | 0 | 0 | 0 | 10 | 4 | 100 | 0.8 | 6 | 7 | 4 |
| Formula 9 | 80 | 1 | 5 | 3 | 5 | 5 | 0 | 1 | 100 | 0.8 | 6 | 6 | 4 |
| Formula 10 | 80 | 1 | 5 | 0 | 5 | 5 | 0 | 4 | 100 | 0.8 | 6 | 6 | 5 |
| Formula 11 | 80 | 1 | 5 | 0 | 0 | 5 | 5 | 4 | 100 | 0.8 | 6 | 6 | 4 |
| Formula 12 | 0 | 5 | 5 | 5 | 0 | 0 | 0 | 85 | 100 | 0 | 0 | 0 | 0 |
| Formula 13 | 0 | 2.5 | 5 | 5 | 0 | 0 | 0 | 87.5 | 100 | 0 | 0 | 0 | 0 |
| Formula 14 | 0 | 5 | 5 | 2.5 | 0 | 0 | 0 | 87.5 | 100 | 0 | 0 | 0 | 0 |
| Formula 15 | 0 | 2.5 | 2.5 | 2.5 | 0 | 0 | 0 | 92.5 | 100 | 0 | 0 | 0 | 0 |
| Formula 16 | 0 | 1 | 5 | 0 | 10 | 0 | 0 | 84 | 100 | 0 | 0 | 0 | 0 |
| Formula 17 | 0 | 1 | 5 | 3 | 10 | 0 | 0 | 81 | 100 | 0 | 0 | 0 | 0 |
| Formula 18 | 0 | 1 | 5 | 0 | 0 | 10 | 0 | 84 | 100 | 0 | 0 | 0 | 0 |
| Formula 19 | 0 | 1 | 5 | 0 | 0 | 0 | 10 | 84 | 100 | 0 | 0 | 0 | 0 |
| Formula 20 | 0 | 1 | 5 | 3 | 5 | 5 | 0 | 81 | 100 | 0 | 0 | 0 | 0 |
| Formula 21 | 0 | 1 | 5 | 0 | 5 | 5 | 0 | 84 | 100 | 0 | 0 | 0 | 0 |
| Formula 22 | 0 | 1 | 5 | 0 | 0 | 5 | 5 | 84 | 100 | 0 | 0 | 0 | 0 |
| Formula 23 | 100 | 0 | 0 | 0 | 0 | 0 | 0 | 0 | 125 | 0.8 | 3 | 1 | 0 |
| Formula 24 | 100 | 0 | 0 | 0 | 0 | 0 | 0 | 0 | 20 | 5 | 7 | 4 | 2 |

TABLE 10-continued

Test Example 10: Mixed Assistants

| No. | Preventive Value Index | | | | | | | | | | | |
|---|---|---|---|---|---|---|---|---|---|---|---|---|
| | CPM | BPM | WR | VR | SR | GM | B | CA | AS | SLB | CBS | CSR |
| Formula 1 | 4 | 4 | 5 | 3 | 4 | 4 | 4 | 5 | 4 | 3 | 3 | 4 |
| Formula 2 | 3 | 3 | 5 | 4 | 3 | 5 | 4 | 5 | 4 | 3 | 3 | 4 |
| Formula 3 | 4 | 5 | 5 | 3 | 3 | 4 | 4 | 5 | 5 | 3 | 3 | 3 |
| Formula 4 | 4 | 4 | 3 | 2 | 4 | 4 | 3 | 3 | 5 | 4 | 2 | 1 |
| Formula 5 | 4 | 3 | 5 | 4 | 3 | 5 | 4 | nt | nt | 4 | 3 | nt |
| Formula 6 | 4 | 3 | 5 | 4 | 4 | 5 | 4 | nt | nt | 3 | 3 | nt |
| Formula 7 | 2 | 3 | 5 | 4 | 4 | 5 | 4 | nt | nt | 3 | 3 | nt |
| Formula 8 | 3 | 3 | 5 | 4 | 3 | 5 | 4 | nt | nt | 3 | 3 | nt |
| Formula 9 | 4 | 3 | 5 | 4 | 3 | 5 | 4 | nt | nt | 3 | 3 | nt |
| Formula 10 | 4 | 4 | 5 | 4 | 3 | 5 | 5 | nt | nt | 3 | 3 | nt |
| Formula 11 | 4 | 4 | 5 | 4 | 3 | 5 | 5 | nt | nt | 3 | 3 | nt |
| Formula 12 | 0 | 0 | 0 | 0 | 0 | 0 | 0 | 0 | 0 | 0 | 0 | 0 |
| Formula 13 | 0 | 0 | 0 | 0 | 0 | 0 | 0 | 0 | 0 | 0 | 0 | 0 |
| Formula 14 | 0 | 0 | 0 | 0 | 0 | 0 | 0 | 0 | 0 | 0 | 0 | 0 |
| Formula 15 | 0 | 0 | 0 | 0 | 0 | 0 | 0 | 0 | 0 | 0 | 0 | 0 |
| Formula 16 | 0 | 0 | 0 | 0 | 0 | 0 | 0 | nt | nt | 0 | 0 | nt |
| Formula 17 | 0 | 0 | 0 | 0 | 0 | 0 | 0 | nt | nt | 0 | 0 | nt |
| Formula 18 | 0 | 0 | 0 | 0 | 0 | 0 | 0 | nt | nt | 0 | 0 | nt |
| Formula 19 | 0 | 0 | 0 | 0 | 0 | 0 | 0 | nt | nt | 0 | 0 | nt |
| Formula 20 | 0 | 0 | 0 | 0 | 0 | 0 | 0 | nt | nt | 0 | 0 | nt |
| Formula 21 | 0 | 0 | 0 | 0 | 0 | 0 | 0 | nt | nt | 0 | 0 | nt |
| Formula 22 | 0 | 0 | 0 | 0 | 0 | 0 | 0 | nt | nt | 0 | 0 | nt |
| Formula 23 | 1 | 1 | 0 | 0 | 0 | 0 | 0 | 0 | 0 | 0 | 0 | 0 |
| Formula 24 | 7 | 6 | 1 | 1 | 1 | 1 | 1 | 1 | 1 | 1 | 0 | 0 |

| | | | |
|---|---|---|---|
| Assistant A | Alkylbenzene sulfonate | (Sodium dodecyl benzene sulfonate) | Neopelex No. 6F |
| Assistant B | Alkyl sulfate | (Sodium lauryl sulfate) | Emal 10PT |
| Assistant C | Alkyl naphthalene sulfonate | (Sodium alkyl naphthalene sulfonate formalin condensate) | Morwet D425 |
| Assistant D | Alkyl naphthalene sulfonate | (Sodium naphthalene sulfonate formalin condensate) | Raberin FAN |
| Assistant E | Alkyl naphthalene sulfonate | (Sodium β-naphthalene sulfonate formalin condensate) | Demol RN |
| Assistant F | Phenol sulfonate | (Sodium phenol sulfonate formalin condensate) | Demol DN |
| Assistant G | Lactose | | Meggletose B 200 |

Preventive Value Indices
7: Preventive value of 100
6: Preventive value of 98 to less than 100
5: Preventive value of 95 to less than 98
4: Preventive value of 90 to less than 95
3: Preventive value of 80 to less than 90
2: Preventive value of 60 to less than 80
1: Preventive value of 30 to less than 60
0: Preventive value of less than 30

[Test Example 11] Evaluation of Compositions Containing D-Tagatose and Anionic Surfactants Against Soil Disease (*Pythium* Red Blight)

The effects of the D-tagatose water-soluble powders containing anionic surfactant prepared in Example 11 on grass red blight were evaluated. Test plants (grass variety: Bentgrass) were planted, and three weeks later, cut to a height of 1 cm prior to use in the test. In the test, after inoculating the seedlings with *Pythium aphanidermatum* preliminarily cultured in wheat bran medium, dilutions obtained by diluting each formula 100-fold with well water were used to treat soil by irrigating at 3 L/m$^2$ (treatment concentrations: D-tagatose 0.8%+assistant 0.2%). After investigating the onset of disease five days after inoculation, control values were calculated from the diseased area. Effects were evaluated using the same evaluation method as Test Example 10. Those results are shown in Table 11-1.

Although all of the test assistants alone demonstrated hardly any control effects against bentgrass red blight, each of the formulas containing D-tagatose and anionic surfactant selected from aryl sulfonates, alkyl sulfates and sulfosuccinates demonstrated remarkable improvement in control effects in comparison with a formula containing D-tagatose only.

(Cabbage Damping-Off)

The effects of the D-tagatose water-soluble powders containing anionic surfactant prepared in Example 11 on cabbage fruit rot were evaluated. Test soil was inoculated by contacting with *Pythium ultimum* preliminarily cultured in wheat bran medium followed by planting the test plants (cabbage variety: Shikidori) therein. The soil was treated by irrigating at 3 L/m$^2$ with the formulations which had been 80-fold diluted with well water (treatment concentrations: D-tagatose 1%+assistant 0.25%). 14 days after inoculation, protective values were calculated from the diseased seedling ratio by defining those seedlings that failed to sprout or exhibited damping-off of the seedling following germination as diseased seedlings. Effects were evaluated using the same evaluation method as Test Example 1. Those results are shown in Table 11-2. The protective value with respect to cabbage damping-off of a formula containing D-tagatose only was 29.9.

All of the formulas containing D-tagatose and an anionic surfactant selected from aryl sulfonates, formalin condensates of aryl sulfonates, alkyl sulfates, polycarboxylates and sulfosuccinates demonstrated remarkable improvement in control effects against cabbage damping-off in comparison with the formula containing D-tagatose only.

TABLE 11-1

Test Example 11: Soil Disease Control Effects by Soil Irrigation Treatment
Bentgrass Red Blight Control Effects

| D-Tagatose Content (parts) | Assistant | | Product Name | Supplier | Assistant Content (parts) | Preventive Value Indices |
|---|---|---|---|---|---|---|
| 80 | Alkyl benzene sulfonate | (Sodium dodecyl benzene sulfonate) | Neopelex No. 6F | Kao Corp. | 20 | 7 |
| 80 | Alkyl sulfate | (Sodium lauryl sulfate) | Emal 10PT | Kao Corp. | 20 | 3 |
| 80 | Dialkyl sulfosuccinate | | Gelopon SDS | Rhodia Nikka Ltd. | 20 | 7 |
| 80 | Dialkyl sulfosuccinate | | Newcol 291PGPM | Nippon Nyukazai Co., Ltd. | 20 | 7 |
| (Comparative Example) No main agent | Alkyl benzene sulfonate | (Sodium dodecyl benzene sulfonate) | Neopelex No. 6F | Kao Corp. | 20 | 0 |
| (Comparative Example) No main agent | Alkyl sulfate | (Sodium lauryl sulfate) | Emal 10PT | Kao Corp. | 20 | 0 |
| (Comparative Example) No main agent | Dialkyl sulfosuccinate | | Gelopon SDS | Rhodia Nikka Ltd. | 20 | 0 |
| (Comparative Example) No main agent | Dialkyl sulfosuccinate | | Newcol 291PGPM | Nippon Nyukazai Co., Ltd. | 20 | 0 |
| (Comparative Example) 80 | Main agent only, no assistant | | | | 0 | 1 |

Preventive Value Indices
7: Preventive value of 100
6: Preventive value of 98 to less than 100
5: Preventive value of 95 to less than 98
4: Preventive value of 90 to less than 95
3: Preventive value of 80 to less than 90
2: Preventive value of 60 to less than 80
1: Preventive value of 30 to less than 60
0: Preventive value of less than 30

TABLE 11-2

Cabbage Damping-off Control Effects

| D-Tagatose Content (parts) | Assistant | | Product Name | Supplier | Assistant Content (parts) | Evaluation Score |
|---|---|---|---|---|---|---|
| 80 | Alkyl benzene sulfonate | (Sodium dodecyl benzene sulfonate) | Neopelex No. 6F | Kao Corp. | 20 | 5 |
| 80 | Alkyl naphthalene sulfonate formalin condensate | (Sodium alkyl naphthalene sulfonate formalin condensate) | Morwet D425 | Lion Akzo Co., Ltd. | 20 | 4 |
| 80 | Alkyl sulfate | (Sodium lauryl sulfate) | Emal 10PT | Kao Corp. | 20 | 4 |
| 80 | Dialkyl sulfosuccinate | | Gelopon SDS | Rhodia Nikka Ltd. | 20 | 5 |
| 80 | Polycarboxylate | (Sodium acrylic/maleic copolymer) | Sokalan CP5 | BASF Corp. | 20 | 3 |
| 80 | Dialkyl sulfosuccinate | | Newcol 291PGPM | Nippon Nyukazai Co., Ltd. | 20 | 5 |

Evaluation Score
5: Improvement in preventive value of 40 or more
4: Improvement in preventive value of 30 to less than 40
3: Improvement in preventive value of 20 to less than 30
2: Improvement in preventive value of 10 to less than 20
1: Improvement in preventive value of 1 to less than 10
0: Equal or decrease in preventive value

[Test Example 12] Evaluation of Compositions Containing D-Tagatose, Sugar, Amino Acid, Salt and Multiple Types of Surfactants (Liquid Preparations) (Mixed Assistants)

Enhancement of the efficacy of 1) a formula containing D-tagatose only, 2) a formula containing D-tagatose and a sugar, amino acid or salt (Assistant 1), 3) a formula containing D-tagatose, and a sugar, amino acid or salt (Assistant 1), and an anionic surfactant selected from aryl sulfonates, formalin condensates of aryl sulfonates and alkyl sulfates (Assistant 2), 4) a formula not containing D-tagatose and containing only an anionic surfactant selected from aryl sulfonates, formalin condensates of aryl sulfonates and alkyl sulfates (Assistant 2), and 5) a formula containing D-tagatose and an anionic surfactant selected from aryl sulfonates, formalin condensates of aryl sulfonates and alkyl sulfates prepared in Example 12 against cucumber downy mildew, grape vine downy mildew and cucumber powdery mildew was evaluated using the same evaluation method as Test Example 10 based on the control value of a 10-fold dilution (treatment concentrations: D-tagatose 0.5%+Assistant 1 0.5%, D-tagatose 0.5%+Assistant 1 0.5%+Assistant 2: aryl sulfonate 0.0016%, formalin condensate of aryl sulfonate 0.03%, alkyl sulfate 0.03%). Those results are shown in Table 12.

Improvement of control effects against cucumber downy mildew, grape vine downy mildew and cucumber powdery mildew was observed with formulas containing as Assistant 1 a specific sugar (monosaccharide, disaccharide, trisaccharide, monosaccharide alcohol, disaccharide alcohol, or amino sugar), an amino acid or a salt (sodium salt, potassium salt, calcium salt, magnesium salt or ammonium salt) with respect to the formula containing D-tagatose only. Moreover, remarkable improvement of control effects was observed by adding a trace amount of Assistant 2 in the form of an anionic surfactant selected from aryl sulfonates, formalin condensates of aryl sulfonates and alkyl sulfates to D-tagatose and Assistant 1 selected from a specific sugar (monosaccharide, disaccharide, trisaccharide, monosaccharide alcohol, disaccharide alcohol or amino sugar), amino acid and salt. The degree of that improvement was more remarkable in comparison with having added Assistant 2 to the formula containing D-tagatose only, and the use of both Assistant 1 and Assistant 2 was found to remarkably enhance the disease control effects of D-tagatose. On the other hand, hardly any effects were demonstrated against each of the diseases by the formula containing Assistant 2 only.

TABLE 12

Test Example 12: Mixtures of Sugar, Amino Acid, Salt and Surfactant

| Broad Classification | Intermediate Classification | Compound Name (Assistant 1) | Main Agent Content (parts) (D-tagatose) | Assistant Content (parts) (Assistant 1) | Protective Value Index CDM | | Protective Value Index VDM | | Protective Value Index CPM | |
|---|---|---|---|---|---|---|---|---|---|---|
| | | | | | Assistant 1 | Assistants 1 + 2 | Assistant 1 | Assistants 1 + 2 | Assistant 1 | Assistants 1 + 2 |
| Sugar | Monosaccharide | L-arabinose | 5 | 5 | 2 | 6 | 2 | 3 | 3 | 7 |
| | | 2-deoxy-D-ribose | 5 | 5 | 4 | 5 | 2 | 4 | 3 | 3 |
| | | D-fructose | 5 | 5 | 3 | 6 | 3 | 5 | 3 | 6 |
| | | D-sorbose | 5 | 5 | 3 | 7 | 2 | 5 | 3 | 6 |
| | | D-psicose | 5 | 5 | 3 | 5 | 2 | 4 | 3 | 6 |
| | | D-glucose | 5 | 5 | 2 | 5 | 2 | 4 | 2 | 5 |
| | | D-galactose | 5 | 5 | 3 | 5 | 2 | 4 | 3 | 6 |
| | | D-allose | 5 | 5 | 3 | 5 | 2 | 4 | 2 | 5 |
| | | D-mannose | 5 | 5 | 3 | 7 | 2 | 4 | 3 | 6 |
| | | L-rharnnese | 5 | 5 | 3 | 7 | 2 | 6 | 3 | 7 |
| | Disaccharide | Sucrose | 5 | 5 | 2 | 6 | 2 | 4 | 2 | 6 |
| | | Lactose | 5 | 5 | 3 | 6 | 2 | 4 | 3 | 6 |
| | | Trehalose | 5 | 5 | 3 | 6 | 2 | 3 | 3 | 5 |
| | | Maltose | 5 | 5 | 2 | 4 | 2 | 4 | 3 | 4 |
| | | Cellobiose | 5 | 5 | 2 | 4 | 2 | 3 | 2 | 5 |
| | | Lactulose | 5 | 5 | 2 | 5 | 2 | 4 | 2 | 4 |
| | | Melibiose | 5 | 5 | 2 | 4 | 2 | 3 | 2 | 4 |
| | Trisaccharide | Raffinose | 5 | 5 | 3 | 4 | 2 | 4 | 2 | 3 |
| | Monosaccharide alcohol | D-talitol | 5 | 5 | 4 | 5 | 2 | 3 | 3 | 3 |
| | | Dulcitol (galactitol) | 5 | 5 | 2 | 5 | 2 | 4 | 2 | 3 |
| | Disaccharide alcohol | Isomalt (palatinit) | 5 | 5 | 4 | 5 | 3 | 3 | 3 | 5 |
| | | Lactitol | 5 | 5 | 4 | 5 | 3 | 4 | 3 | 4 |
| | Amino sugar | D-glucosamine hydrochloride | 5 | 5 | 4 | 5 | 4 | 4 | 3 | 4 |
| | | D-galactosamine hydrochloride | 5 | 5 | 4 | 5 | 3 | 4 | 4 | 5 |
| Amino Acid | Amine acid | Glycine | 5 | 5 | 5 | 6 | 2 | 3 | 3 | 4 |
| | | β-alanine | 5 | 5 | 5 | 6 | 2 | 3 | 4 | 6 |
| | | L-glutamic acid | 5 | 5 | 5 | 7 | 3 | 4 | 3 | 5 |
| | | L-asoartio acid | 5 | 5 | 5 | 6 | 2 | 5 | 2 | 4 |
| | | L-alanine | 5 | 5 | 3 | 6 | 3 | 3 | 3 | 5 |
| | | L-histidine | 5 | 5 | 3 | 5 | 2 | 4 | 3 | 4 |
| | | L-leucine | 5 | 5 | 3 | 6 | 2 | 4 | 2 | 4 |
| | | L-valine | 5 | 5 | 3 | 6 | 2 | 4 | 2 | 4 |
| | | L-ornithine | 5 | 5 | 3 | 5 | 2 | 4 | 3 | 4 |
| | | L-phenylalanine | 5 | 5 | 3 | 4 | 2 | 3 | 2 | 3 |
| | | L-cysteine | 5 | 5 | 3 | 4 | 2 | 4 | 3 | 3 |
| | | L-arginine | 5 | 5 | 2 | 3 | 2 | 3 | 4 | 3 |
| | | L-asparagine | 5 | 5 | 2 | 3 | 2 | 3 | 3 | 3 |
| | | L-glutamine | 5 | 5 | 2 | 3 | 2 | 3 | 2 | 3 |
| Salt | Sodium salt | NaCl | 5 | 5 | 5 | 7 | 2 | 3 | 4 | 4 |
| | | Na2SO4 | 5 | 5 | 3 | 7 | 2 | 5 | 4 | 4 |
| | | NaHCO3 | 5 | 5 | 3 | 6 | 2 | 3 | 4 | 4 |
| | | Na2CO3 | 5 | 5 | 3 | 6 | 2 | 3 | 4 | 4 |
| | | NaNO3 | 5 | 5 | 3 | 6 | 2 | 5 | 4 | 4 |
| | | Na2HPO4 | 5 | 5 | 4 | 6 | 2 | 4 | 4 | 4 |
| | | CHSCOONa | 5 | 5 | 3 | 6 | 2 | 3 | 2 | 4 |
| | Potassium salt | KCl | 5 | 5 | 4 | 7 | 2 | 3 | 3 | 8 |
| | | K2CO3 | 5 | 5 | 4 | 6 | 2 | 3 | 2 | 3 |
| | | K2SO4 | 5 | 5 | 3 | 7 | 2 | 4 | 3 | 4 |
| | | KNO3 | 5 | 5 | 2 | 7 | 2 | 3 | 3 | 4 |
| | | KH2PO4 | 5 | 5 | 4 | 6 | 2 | 3 | 3 | 4 |
| | | K3PO4 | 5 | 5 | 4 | 4 | 3 | 3 | 2 | 3 |
| | | CH3COOK | 5 | 5 | 4 | 5 | 3 | 3 | 2 | 3 |
| | Calcium salt | CaCl2 | 5 | 5 | 3 | 4 | 2 | 3 | 2 | 2 |
| | | Ca(NO3)2 | 5 | 5 | 3 | 6 | 3 | 5 | 2 | 2 |
| | | CaSO4 | 5 | 5 | 3 | 5 | 2 | 3 | 2 | 2 |
| | | CaCO3 | 5 | 5 | 3 | 5 | 2 | 3 | 2 | 4 |

TABLE 12-continued

Test Example 12: Mixtures of Sugar, Amino Acid, Salt and Surfactant

|  |  |  |  |  |  |  |  |  |  |
|---|---|---|---|---|---|---|---|---|---|
| Magnesium salt | MgCl2 | 5 | 5 | 4 | 7 | 3 | 5 | 3 | 4 |
|  | MgSO4 | 5 | 5 | 4 | 6 | 2 | 3 | 4 | 5 |
| Ammonium salt | NH4Cl | 5 | 5 | 4 | 6 | 4 | 5 | 3 | 6 |
|  | NH4NO3 | 5 | 5 | 4 | 6 | 4 | 5 | 3 | 6 |
|  | (NH4)2SO4 | 5 | 5 | 4 | 6 | 3 | 4 | 4 | 4 |
|  | NH4H2PO4 | 5 | 5 | 2 | 3 | 2 | 4 | 3 | 5 |
|  | (NH4)2HPO4 | 5 | 5 | 4 | 3 | 3 | 3 | 3 | 5 |
|  | None | 5 | 0 | 2 | — | 1 | — | 2 | — |
|  | None (main agent + Assistant 2) | 5 | 0 | — | 3 | — | 2 | — | 3 |
|  | None (no main agent, Assistant 2 only) | 0 | 0 | — | 1 | — | 0 | — | 0 |

Assistant 2 Composition

|  | Intermediate Classification | Narrow Classification | Product Name | Assistant Content |
|---|---|---|---|---|
| Assistant A | Alkyl benzene sulfonate | (Sodium dodecyl benzene sulfonate) | Neopelex No. 6F | 0.016 |
| Assistant B | Alkyl sulfate | (Sodium lauryl sulfate) | Emal 10PT | 0.313 |
| Assistant C | Alkyl naphthalene sulfonate | (Sodium alkyl naphthalene sulfonate formalin condensate) | Morwet D425 | 0.313 |

Preventive Value Indices
7: Preventive value of 100
5: Preventive value of 98 to less than 100
5: Preventive value of 95 to less than 98
4: Preventive value of 90 to less than 95
3: Preventive value of 80 to less than 90
2: Preventive value of 60 to less than 80
1: Preventive value of 30 to less than 60
0: Preventive value of less than 30

[Test Example 13] Evaluation of Compositions Containing Monosaccharides and Multiple Types of Surfactants (Water-Soluble Powders) (Mixed Assistants)

The effects of 1) a formula containing D-tagatose at 20% or 60% and a sugar selected from D-fructose, D-glucose, D-galactose, D-mannose, D-talose, D-sorbose, D-psicose and lactose, 2) a formula containing D-tagatose at 20% or 60% and an anionic surfactant selected from aryl sulfonates, formalin condensates of aryl sulfonates and alkyl sulfates at 0.25%, 5% and 5%, respectively, in addition to a sugar selected from D-fructose, D-glucose, D-galactose, D-mannose, D-talose, D-sorbose, D-psicose and lactose, 3) a formula containing an anionic surfactant selected from aryl sulfonates, formalin condensates of aryl sulfonates and alkyl sulfates at 0.25%, 5% and 5%, respectively, and 4) a formula containing D-tagatose at 20%, 60% or 80% prepared in Example 13 against cucumber downy mildew, grape vine downy mildew, cucumber powdery mildew and wheat rust were evaluated using the same evaluation method as Test Example 10. Those results are shown in Table 13. Improvement of efficacy against cucumber downy mildew, grape vine downy mildew, cucumber powdery mildew and wheat rust was evaluated based on the control effect of a 200-fold dilution (treatment concentrations: D-tagatose 0.1% to 0.4%, Assistant 0.00125% to 0.025%), while efficacy against wheat rust was evaluated based on the control effect of a 100-fold dilution (treatment concentrations: D-tagatose 0.8%, Assistant 0.0025% to 0.05%).

Formulas containing D-tagatose at 20% or 60% and a sugar selected from D-fructose, D-glucose, D-galactose, D-mannose, D-talose, D-sorbose, D-psicose and lactose demonstrated high control effects in the same manner as formulas containing D-tagatose at 80%. Remarkable improvement in control effects was observed by adding a trace amount of an assistant in the form of an anionic surfactant selected from aryl sulfonates, formalin condensates of aryl sulfonates and alkyl sulfates to compositions containing D-tagatose and each of the aforementioned sugars. The degree of that improvement was more remarkable in comparison with the addition of various sugars to D-tagatose, and the use of an assistant was found to remarkably enhance disease control effects of compositions containing D-tagatose.

TABLE 13

Test Example 12: Mixtures of Various Monosaccharides and Surfactants

| | | | Content | | | Preventive Value Indices | | | | | | | |
|---|---|---|---|---|---|---|---|---|---|---|---|---|---|
| | | | | | | CDM | | VDM | | CPM | | WR | |
| Compound 1 | Compound 2 | Compound 3 | Compound 1 | Compound 2 | Compound 3 | 1 + 2 + 3 | 1 + 2 + 3 assistant | 1 + 2 + 3 | 1 + 2 + 3 assistant | 1 + 2 + 3 | 1 + 2 + 3 assistant | 1 + 2 + 3 | 1 + 2 + 3 assistant |
| D-tagatose | D-glucose | — | 20 | 30 | — | 3 | 6 | 1 | 6 | 2 | 4 | 1 | 4 |
| D-tagatose | D-fructose | — | 20 | 5 | — | 2 | 5 | 1 | 6 | 2 | 3 | 1 | 4 |
| D-tagatose | D-galactose | — | 20 | 15 | — | 2 | 5 | 1 | 6 | 2 | 3 | 1 | 4 |

TABLE 13-continued

Test Example 12: Mixtures of Various Monosaccharides and Surfactants

| D-tagatose | Lactose | — | 20 | 2.5 | — | 2 | 5 | 1 | 6 | 2 | 4 | 1 | 4 |
|---|---|---|---|---|---|---|---|---|---|---|---|---|---|
| D-tagatose | D-glucose | D-galactose | 20 | 30 | 15 | 3 | 6 | 1 | 6 | 3 | 4 | 1 | 4 |
| D-tagatose | D-glucose | D-fructose | 20 | 30 | 5 | 2 | 5 | 1 | 6 | 2 | 3 | 1 | 4 |
| D-tagatose | D-glucose | Lactose | 20 | 30 | 2.5 | 2 | 5 | 1 | 6 | 3 | 3 | 1 | 4 |
| D-tagatose | D-galactose | D-fructose | 20 | 15 | 5 | 2 | 5 | 1 | 6 | 2 | 3 | 1 | 4 |
| D-tagatose | D-galactose | Lactose | 20 | 15 | 2.5 | 2 | 4 | 1 | 5 | 3 | 4 | 1 | 4 |
| D-tagatose | D-fructose | — | 60 | 20 | — | 3 | 6 | 2 | 6 | 3 | 4 | 1 | 4 |
| D-tagatose | D-psicose | — | 60 | 20 | — | 3 | 6 | 2 | 6 | 3 | 4 | 1 | 4 |
| D-tagatose | D-sorbose | — | 60 | 20 | — | 3 | 6 | 1 | 6 | 3 | 4 | 1 | 4 |
| D-tagatose | D-glucose | — | 60 | 20 | — | 3 | 6 | 1 | 6 | 3 | 4 | 1 | 4 |
| D-tagatose | D-galactose | — | 60 | 20 | — | 3 | 6 | 1 | 6 | 2 | 3 | 2 | 4 |
| D-tagatose | D-mannose | — | 60 | 20 | — | 3 | 6 | 1 | 6 | 3 | 4 | 1 | 4 |
| D-tagatose | D-talose | — | 60 | 20 | — | 3 | 6 | 1 | 6 | 3 | 4 | 1 | 4 |
| D-tagatose | — | — | 20 | — | — | 1 | 2 | 0 | 3 | 1 | 2 | 0 | 3 |
| D-tagatose | — | — | 60 | — | — | 2 | 2 | 1 | 3 | 1 | 2 | 1 | 3 |
| D-tagatose | — | — | 80 | — | — | 3 | 6 | 2 | 6 | 2 | 4 | 1 | 4 |
| — | — | Lactose | — | — | 90 | — | 1 | — | 0 | — | 0 | — | 1 |

Assistant Composition

| | Intermediate Classification | Narrow Classification | Product Name | Assistant Content |
|---|---|---|---|---|
| Assistant A | Alkyl benzene sulfonate | (Sodium dodecyl benzene sulfonate) | Neopelex No. 6F | 0.25 |
| Assistant B | Alkyl sulfate | (Sodium lauryl sulfate) | Emal 10PT | 5 |
| Assistant C | Alkyl naphthalene sulfonate | (Sodium alkyl naphthalene sulfonate formalin condensate) | Morwet D425 | 5 |

Preventive Value Indices
7: Preventive value of 100
6: Preventive value of 98 to less than 100
5: Preventive value of 95 to less than 98
4: Preventive value of 90 to less than 95
3: Preventive value of 80 to less than 90
2: Preventive value of 60 to less than 80
1: Preventive value of 30 to less than 60
0: Preventive value of less than 30

INDUSTRIAL APPLICABILITY

The present invention provides a composition for enhancing the plant disease control effects of monosaccharides which comprises a specific nonionic surfactant, specific anionic surfactant, water-soluble polymer, amino acid, amino sugar, disaccharide alcohol or salt, a method for controlling plant disease that uses that composition, and a method for enhancing the control effects of monosaccharides on plant diseases. The composition can be used as a stem and leaf dusting powder, soil treatment agent or seed treatment agent, and is able to control various plant diseases without causing chemical damage to the host plant.

The invention claimed is:

1. A composition comprising 5 to 95 parts by weight of D-tagatose; and at least one or more assistants selected from 0.01 to 5 parts by weight of an alkyl sulfate, 0.01 to 5 parts by weight of an aryl sulfonate and 0.01 to 20 parts by weight of a formalin condensate of an aryl sulfonate, based on a total of 100 parts by weight of the composition.

2. The composition according to claim 1, further comprising a water-soluble polymer, a sugar, an amino acid, an amino sugar, a disaccharide alcohol or a salt at a blending ratio of 0.001 to 40 parts by weight based on 1 part by weight of D-tagatose.

3. The composition according to claim 2, wherein water soluble polymer, sugar, amino acid, amino sugar and disaccharide alcohol is one or more selected from polyoxyalkylene, dextrin, alpha starch, etherified starch, esterified starch, xanthan gum, guar gum, polyvinylpyrrolidone, D-glyceraldehyde, 2-deoxy-D-ribose, D-altrose, L-arabinose, D-fructose, D-sorbose, D-psicose, D-glucose, D-galactose, D-allose, D-mannose, L-rhamnose, sucrose, lactose, trehalose, maltose, cellobiose, lactulose, melibiose, raffinose, D-talitol, dulcitol, glycine, β-alanine, L-glutamic acid, L-aspartic acid, L-alanine, L-histidine, L-leucine, L-valine, L-ornithine, L-phenylalanine, L-cysteine, L-pyroglutamic acid, D-glucosamine hydrochloride, D-galactosamine hydrochloride, lactitol and isomalt; and wherein, in the salt, the cation is derived from a base that forms the salt is at least one or more ions selected from sodium, potassium, ammonium, calcium and magnesium.

4. The composition according to claim 1, which is a control agent for a plant disease.

5. The composition according to claim 4, wherein the plant disease is a disease caused by fungi or a disease caused by bacteria.

6. A method for controlling plant disease, comprising applying the composition according to claim 1 to a plant body.

7. The method for controlling plant disease according to claim 6, wherein application to a plant body is carried out by contacting the composition with a plant body or seed, or by contacting with a root or underground stem of a plant by containing in cultivation soil.

8. The method for controlling plant disease according to claim 7, wherein application to cultivation soil is carried out by treating the surface of soil with the composition, irrigating soil with the composition or mixing the composition into the soil.

9. A method for enhancing the control effects of D-tagatose against plant disease, comprising applying the composition according to claim 1 to a plant body.

10. The composition according to claim 2, which is a control agent for a plant disease.

11. The composition according to claim 10, wherein the plant disease is a disease caused by fungi or a disease caused by bacteria.

12. A method for controlling plant disease, comprising applying the composition according to claim 2 to a plant body.

13. The method for controlling plant disease according to claim 12, wherein application to a plant body is carried out by contacting the composition with a plant body or seed, or by contacting with a root or underground stem of a plant by containing in cultivation soil.

14. The method for controlling plant disease according to claim 13, wherein application to cultivation soil is carried out by treating the surface of soil with the composition, irrigating soil with the composition or mixing the composition into the soil.

15. A method for enhancing the control effects of a D-tagatose against plant disease, comprising applying the composition according to claim 2 to a plant body.

* * * * *